(12) United States Patent
Huang et al.

(10) Patent No.: US 11,548,897 B2
(45) Date of Patent: Jan. 10, 2023

(54) CRYSTALLINE FORMS OF A TRIAZOLOPYRIMIDINE COMPOUND

(71) Applicant: NOVARTIS AG, Basel (CH)

(72) Inventors: Ying Huang, Shanghai (CN); Bo Liu, Shanghai (CN); Liang Mao, Shanghai (CN); Long Wang, Shanghai (CN); Liladhar Murlidhar Waykole, Succasunna, NJ (US); Lijun Zhang, Shanghai (CN)

(73) Assignee: Novartis AG, Basel (CH)

( * ) Notice: Subject to any disclaimer, the term of this patent is extended or adjusted under 35 U.S.C. 154(b) by 5 days.

(21) Appl. No.: 17/371,399

(22) Filed: Jul. 9, 2021

(65) Prior Publication Data

US 2021/0340152 A1 Nov. 4, 2021

Related U.S. Application Data

(62) Division of application No. 16/311,638, filed as application No. PCT/CN2017/089003 on Jun. 19, 2017, now Pat. No. 11,091,489.

(30) Foreign Application Priority Data

Jun. 20, 2016 (WO) ................ PCT/CN2016/086350

(51) Int. Cl.
| | | |
|---|---|---|
| C07D 487/04 | (2006.01) | |
| A61P 35/00 | (2006.01) | |
| A61P 35/02 | (2006.01) | |
| A61K 31/519 | (2006.01) | |

(52) U.S. Cl.
CPC .......... *C07D 487/04* (2013.01); *A61K 31/519* (2013.01); *A61P 35/00* (2018.01); *A61P 35/02* (2018.01); *C07B 2200/13* (2013.01)

(58) Field of Classification Search
CPC .......................... C07D 487/04; C07B 2200/13
See application file for complete search history.

(56) References Cited

U.S. PATENT DOCUMENTS

| | | |
|---|---|---|
| 2,779,780 A | 1/1957 | Middleton |
| 5,621,002 A | 4/1997 | Bosslet et al. |
| 7,563,589 B2 | 7/2009 | Zhang et al. |
| 8,586,313 B2 | 11/2013 | Laird et al. |
| 8,691,507 B2 | 4/2014 | Copeland et al. |
| 8,895,526 B2 | 11/2014 | Stillman et al. |
| 2006/0127408 A1 | 6/2006 | Young et al. |
| 2006/0246505 A1 | 11/2006 | Walther |
| 2006/0287341 A1 | 12/2006 | Wu et al. |
| 2009/0124609 A1 | 5/2009 | Albrecht et al. |
| 2009/0170715 A1 | 7/2009 | Glinsky |
| 2009/0286984 A1 | 11/2009 | Raeppel et al. |
| 2010/0105656 A1 | 4/2010 | Cheng et al. |
| 2010/0137411 A1 | 6/2010 | Green et al. |
| 2011/0009429 A1 | 1/2011 | Oakley et al. |
| 2013/0244256 A1 | 9/2013 | Clarke et al. |
| 2014/0046056 A1 | 2/2014 | Maekawa et al. |
| 2014/0213475 A1 | 7/2014 | Lawrence et al. |
| 2016/0176882 A1 | 6/2016 | Chan et al. |

FOREIGN PATENT DOCUMENTS

| | | |
|---|---|---|
| JP | 2004-238296 | 8/2004 |
| WO | WO 2000/035436 | 6/2000 |
| WO | WO 2001/053834 | 7/2001 |
| WO | WO 2002/006213 | 1/2002 |
| WO | WO 2003/044021 | 5/2003 |
| WO | WO 2003/076424 | 9/2003 |
| WO | WO 2003/077914 | 9/2003 |
| WO | WO 2004/078163 | 9/2004 |
| WO | WO 2006/122806 | 11/2006 |
| WO | WO 2007/014011 | 2/2007 |
| WO | WO 2007/084786 | 7/2007 |
| WO | WO 2009/036082 | 3/2009 |
| WO | WO 2009/055730 | 4/2009 |
| WO | WO 2009/155386 | 12/2009 |
| WO | WO 2010/022076 | 2/2010 |
| WO | WO 2010/064019 | 6/2010 |
| WO | WO 2011/112766 | 9/2011 |
| WO | WO 2012/034132 | 3/2012 |
| WO | WO 2012/118812 | 9/2012 |
| WO | WO 2012/151277 | 11/2012 |
| WO | WO 2013/039988 | 3/2013 |
| WO | WO 2013/049770 | 4/2013 |
| WO | WO 2013/138361 | 9/2013 |
| WO | WO 2014/078813 | 5/2014 |
| WO | WO 2014/100080 | 6/2014 |
| WO | WO 2014/124326 | 8/2014 |
| WO | WO 2014/124418 | 8/2014 |
| WO | WO 2014/144747 | 9/2014 |
| WO | WO 2014/151142 | 9/2014 |
| WO | WO 2014/153030 | 9/2014 |
| WO | WO 2015/103137 | 7/2015 |
| WO | WO 2015/123365 | 8/2015 |

(Continued)

OTHER PUBLICATIONS

Alajez et al., "Enhancer of Zeste Homolog 2 (EZH2) is Overexpressed in Recurrent Nasopharyngeal Carcinoma and is Regulated by miR-26a, miR-101, and miR-98" *Cell Death and Disease* 1:e85, 2010.
Bai et al., "Inhibition Enhancer of Zeste Homologue 2 Promotes Senescence and Apoptosis Induced by Doxorubicin in p53 Mutant Gastric Cancer Cells" *Cell Prolif* 47(3):211-218, 2014.
Béguelin et al., "EZH2 Is Required for Germinal Center Formation and Somatic EZH2 Mutations Promote Lymphoid Transformation" *Cancer Cell* 23(5):677-692, May 13, 2013.
Bender et al., Reduced H3K27me3 and DNA Hypomethylation are Major Drivers of Gene Expression in K27M Mutant Pediatric High-Grade Gliomas *Cancer Cell* 24(5):660-672, Nov. 11, 2013.

(Continued)

*Primary Examiner* — Susanna Moore

(74) *Attorney, Agent, or Firm* — Daniel E. Raymond

(57) ABSTRACT

Provided herein are crystalline forms of a triazolopyrimidine compound, which is useful for treating a PRC2-mediated disease or disorder.

4 Claims, 11 Drawing Sheets

(56) References Cited

FOREIGN PATENT DOCUMENTS

| WO | WO 2016/075289 | 5/2016 |
|---|---|---|
| WO | WO 2016/096907 | 6/2016 |
| WO | WO 2016/102272 | 6/2016 |
| WO | WO 2016/103155 | 6/2016 |
| WO | WO 2016/106138 | 6/2016 |

OTHER PUBLICATIONS

Bhan et al., "Histone Methyltransferase EZH2 Is Transcriptionally Induced by Estradiol as Well as Estrogenic Endocrine Disruptors Bisphenol-A and Diethylstilbestrol" *Journal of Molecular Biology* 426(20):3426-3441, Oct. 9, 2014.
Bilter et al., "Synthetic Lethality by Targeting EZH2 Methyitransferase Activily inARIDIA-Mutated Cancers" *Nat Med* 21(3):231-238, Mar. 2015.
Borbone et al., "Enhancer of Zeste Homolog 2 Overexpression Has a Role in the Development of Anaplastic Thyroid Carcinomas" *The Journal of Clinical Endocrinology and Metabolism* 96(4):1029-1038, Aug. 2011.
Chang et al., "EZH2 Promotes Expansion of Breast Tumor Initiating Cells through Activation of RAF1-β-Catenin Signaling" *Cancer Cell* 19(1):86-100, 2011.
Chen et al., "Cyclin-Dependent Kinases Regulate Epigenetic Gene Silencing Through Phosphorylation of EZH2" *Nat. Cell Boil.* 12(11):1108-1114, 2010.
Chen et al., "JNK and STAT3 Signaling Pathways Converge on Akt-Mediated Phosphorylation of EZH2 in Bronchial Epithelial Cells Induced by Arsenic" *Cell Cycle* 12(1):112-121, 2013.
Ciarapica et al., "Pharmacological Inhibition of EZH2 as a Promising Differentiation Therapy in Embryonal RMS" *BMC Cancer* 14:139, Feb. 27, 2014.
Dai et al., "Comparative Methylome Analysis in Solid Tumors Reveals Aberrant Methylation at Chromosome 6p in Nasopharyngeal Carcinoma" *Cancer Medicine* 4(7):1079-1090, Jul. 2015.
Ding et al., "The Polycomb Group Protein Enhancer of Zeste 2 is a Novel Therapeutic Target for Cervical Cancer" *Clinical and Experimental Pharmacology and Physiology* 42:458-464, 2015.
Formenko et al., "Robust regression for high throughput drug screening" *Computer Methods and Programs in Biomedicine* 82:31-37. 2006.
Gonzalez et al., "Histone Methyltransferase EZH2 Induces Akt-Dependent Genomic Instability and BRCA1 Inhibition in Breast Cancer" *Cancer Research* 71(6):2360-2370, 2011.
Hebbard et al., "Control of Mammary Tumor Differentiation by SKI-606 (bosutinib)" *Oncogene* 30(3):301-312, 2011.
Huang, "Discovery of First-in-Class, Potent, and Orally Bioavailable Embryonic Ectoderm Development (EED) Inhibitor with Robust Anticancer Efficacy" *Journal of Medicinal Chemistry* 60:2215-2226, Jan. 2017.
Kahm, "grofit: Fitting Biologial Growth Curves with R" *Journal of Statistical Software* 33(7):1-12, 2010.
Katona et al., "EZH2 Inhibition Enhances the Efficacy of an EGFR Inhibitor in Suppressing Colon Cancer Cells" *Cancer Biol. Ther* 15(12):1677-1687, 2014.
Kelly et al., "Monotone Smoothing with Application to Dose-Response Curves and the Assessment of Synergism" *Biometrics* 46(4):1071-1085, 1990.
Kim et al., "Phosphorylation of EZH2 Activates STAT3 Signaling via STAT3 Methylation and Promotes Tumorigenicity of Glioblastoma Stem-Like Cells" *Cancer Cell* 23 (6):839-852, Jun. 10, 2013.
Kim et al., "SWI/SNF-Mutant Cancers Depend on Catalytic and Non-Catalytic Activity of EZH2" *Nat. Med* 21(12):1491-1496, Dec. 2015.
Knutson et al., "Durable Tumor Regression in Genetically Altered Malignant Rhabdoid Tumors by Inhibition of Methyltransferase EZH2" *Proc. Natl. Acad. Sci USA* 110(19):7922-7927, May 7, 2013.
Knutson et al., "Synergistic Anti-Tumor Activity of EZH2 Inhibitors and Glucocorticoid Receptor Agonists in Models of Germinal Center Non-Hodgkin Lymphomas" *PLOS One* pp. 1-22, Dec. 10, 2014.
Lafave et al., "Loss of BAP1 Function Leads to EZH2-Dependent Transformation" *Nature Medicine* 21(11):1344-1349, 2015.
Lin et al., "The Genomic Landscape of Nasopharyngeal Carcinoma" *Nature Genetics* 46(8):866-871, 2014.
Liu et al., "EZH2-Mediated Loss of miR-622 Determines CXCR4 Activation in Hepatocellular Carcinoma" *Nature Communications* 6:8494 Sep. 25, 2015.
Mallen-St Clair et al., "EZH2 Couples Pancreatic Regeneration to Neoplastic Progression" *Genes Dev* 26(5):439-444, Mar. 2012.
Marchesi et al. "The ablation of EZH2 Uncovers its Crucial Role in Rhabdomyosarcoma Formation" *Cell Cycle* 11(20):3828-3836, Oct. 15, 2012.
Margueron et al., "Role of the Poly comb Protein EED in the Propagation of Repressive Histone Marks" *Nature* 461(7265):762-767, Oct. 8, 2009.
Mccabe et al., "EZH2 Inhibition as a Therapeutic Strategy for Lymphoma with EZH2-Activating Mutations" *Nature* 492(7427):108-112, Dec. 6, 2012.
Meng et al., "The Prognostic Role of EZH2 Expression in Rectal Cancer Patients Treated with Neoadjuvant Chemoradiotherapy" *Radiat Oncol.* 9:188, Aug. 27, 2014.
Moore et al., "EZH2 Inhibition Decreases p38 Signaling and Suppresses Breast Cancer Motility and Metastasis" *Breast Cancer Res Treat* 138(3):741-752, Apr. 2013.
Morin et al., "Somatic Mutations Altering EZH2 (Tyr641) in Follicular and Diffuse large B-Cell Lymphomas of Germinal-Center Origin" *Nat Genet* 42(2):181-185, Jan. 17, 2010.
Musch et al., "Nucleoside Drugs Induce Cellular Differentiation by Caspase-Dependent Degradation of Stem Cell Factors" *PLoS One* 5(5):e10726, May 19, 2010.
Nagarsheth et al., "PRC2 Epigenetically Silences Th1-Type Chemokines to Suppress Effector T-Cell Trafficking in Colon Cancer" *Cancer Research* 76(2):275-282, Jan. 15, 2016.
Nakagawa et al., "Epigenetic Therapy with the Histone Methyltransferase EZH2 Inhibitor 3-Deazaneplanocin A Inhibits the Growth of Cholangiocarcinoma Cells" *Oncol Rep* 31(2):983-988, Feb. 2014.
Ning et al., "DNMT1 and EZH2 Mediated Methylation Silences the MicroRNA-200b/a/429 Gene and Promotes Tumor Progression" *Cancer Lett* 359(2):198-205, Apr. 10, 2015.
Hassan et al., "Heterocyclic Synthesis via Enaminones: Synthesis and Molecular Docking Studies of Some Novel Heterocyclic Compounds Containing Sulfonamide Moieiy" *International Journal of Organic Chemistry* 4:68-81, 2014.
Normolle, "An Algorithn for Robust Non-Linear Analysis of Radioimmnoassays and Other Bioassays" *Statistics in Medicine* 12:2025-2042, 1993.
Pathiraja et al., "Epigenetic Reprogramming of HOXC10 in Endocrine-Resistant Breast Cancer" *Sci Transl Med.* 6(229):229ra41, Mar. 26, 2014.
Peng et al. "Epigenetic Silencing of $T_H1$-Type Chemokines Shapes Tumour Immunity and Immunotherapy" *Nature* (7577):249-53, Nov. 12, 2015.
Popovic et al., "Histone Methyltransferase MMSET/NSD2 Alters EZH2 Binding and Reprograms the Myeloma Epigenome through Global and Focal Changes in H3K36 and H3K27 Methylation" *PLoS Genet* 10(9):e1004566, Sep. 4, 2014.
Richter et al., "EZH2 is a Mediator of EWS/FLI1 Driven Tumor Growth and Metastasis Blocking Endothelial and Neuro-Ectodermal Differentiation" *Proc. Natl. Acad. Sci. USA* 106(13):5324-5329, Mar. 31, 2009.
Rietzler et al., "The Human WD Repeat Protein WAIT-1 Specifically Interacts with the Cytoplasmic Tails of β7-Integrins" *Journal of Biological Chemistry* 273:27459-27466, Oct. 16, 1998.
Rojanasakul, "Linking JNK-STAT3-Akt Signaling Axis to EZH2 Phosphorylation" *Cell Cycle* 12(2):202-203, 2013.
Schumacher et al., "The Murine Polycomb-Group Geneeedand Its Human Orthologue: Functional Implications of Evolutionary Conservation" *Genomics* 54(1):79-88, Nov. 15, 1998.

(56) References Cited

OTHER PUBLICATIONS

Sebaugh, "Guidelines for accurate EC50/IC50 estimation" *Pharmaceutical Statistics* 10:128-134, 2011.
Sewalt et al., "Characterization of Interactions between the Mammalian Polycomb-Group Proteins Enx1/EZH2 and EED Suggests the Existence of Different Mammalian Polycomb-Group Protein Complexes" *Molecular and Cellular Biology* 18(6):3586-3595, Jun. 1998.
Sharma et al., "Bridging Links between Long Noncoding RNA Hotair and HPV Oncoprotein E7 in Cervical Cancer Pathogenesis" *Sci Rep* 5:11724, 2015.
Sinha et al., "Mutant WT1 is Associated with DNA Hypermethylation of PRC2 Targets in AML and Responds to EZH2 Inhibition" *Blood* 125(2):316-326, Jan. 8, 2015.
Svedlund et al., "The Histone Methyltransferase EZH2, an Oncogene Common to Benign and Malignant Parathyroid Tumors" *Endocrine-Related Cancer* 21(2):231-239, Feb. 27, 2014.
Gibaja et al., "Development of Secondary Mutations in Wild-Type and Mutant EZH2 Alleles Cooperates to Confer Resistance to EZH2 Inhibitors" *Oncogene* 1-9, Apr. 20, 2015.
Qi et al., "Selective Inhibition of Ezh2 by a Small Molecule Inhibitor Blocks Tumor Cells Proliferation" *Proc. Natl. Acad. Sci. USA* 109(52):21360-21365, Dec. 26, 2012.
Tanaka et al., "Ewing's Sarcoma Precursors are Highly Enriched in Embryonic Osteochondrogenic Progenitors" *Journal Clinical Investigation* 124(7):3061-3074, Jul. 2014.
Tang et al., "Pharmacologic Down-Regulation of EZH2 Suppresses Bladder Cancer in vitro andin vivo" *Oncotarget* 5(21):10342-10355, Nov. 15, 2014.
Tiffen et al., "Targeting Activating Mutations of EZH2 Leads to Potent Cell Growth Inhibition in Human Melanoma by Derepression of Tumor Suppressor Genes" *Onocotarget* 6(29):27023-27036, Sep. 29, 2015.
Tong et al., "EZH2 Supports Nasopharyngeal Carcinoma Cell Aggressiveness by Forming a Co-Repressor Complex with HDAC1/HDAC2 and Snail to Inhibit E-Cadherin" *Oncogene* 31:583-594, 2012.
Varambally "The Polycomb Group Protein EZH2 is Involved in Progression of Prostate Cancer" *Nature* 419(6907):624-629, Oct. 10, 2002.
Wagener et al., "Enhancer of Zeste Homolog 2 (EZH2) Expression is an Independent Prognostic Factor in Renal Cell Carcinoma" *BMC Cancer* 10:524, Oct. 4, 2010.
Wang et al., "EZH2 Mediates Epigenetic Silencing of Neuroblastoma Suppressor Genes CASZ1,CLU,RUNX3, and NGFR" *Cancer Research* 72(1):315-324, Jan. 1, 2012.
Wu et al., "Polycomb Protein EZH2 Regulates Cancer Cell Fate Decision in Response to DNA Damage" *Cell Death and Differentiation* 18:1771-1779, 2011.
Xu et al., "Selective Inhibition of EZH2 and EZH1 Enzymatic Activity by a Small Molecule Suppresses MLL-Rearranged Leukemia" *Blood* 125(2):346-357, Jan. 8, 2015.
Yamaguchi et al., "Histone Deacetylase Inhibitor (SAHA) and Repression of EZH2 Synergistically Inhibit Proliferation of Gallbladder Carcinoma" 101(2):355-362, Feb. 2010.
Yan et al., "IKKa restoration via EZH2 Suppression Induces Nasopharyngeal Carcinoma Differentiation" *Nature Communications* 5:3661, 2014.
Zeng et al., "Phosphorylation of EZH2 by CDK1 and CDK2" *Cell Cycle* 10(4):578-583, 2011.
Zhang et al., "EZH2-miR-30d-KPNB1 Pathway Regulates Malignant Peripheral Nerve Sheath Tumour Cell Survival and Tumourigenesis" *Journal of Pathology* 232(3):308-318, Feb. 2014.

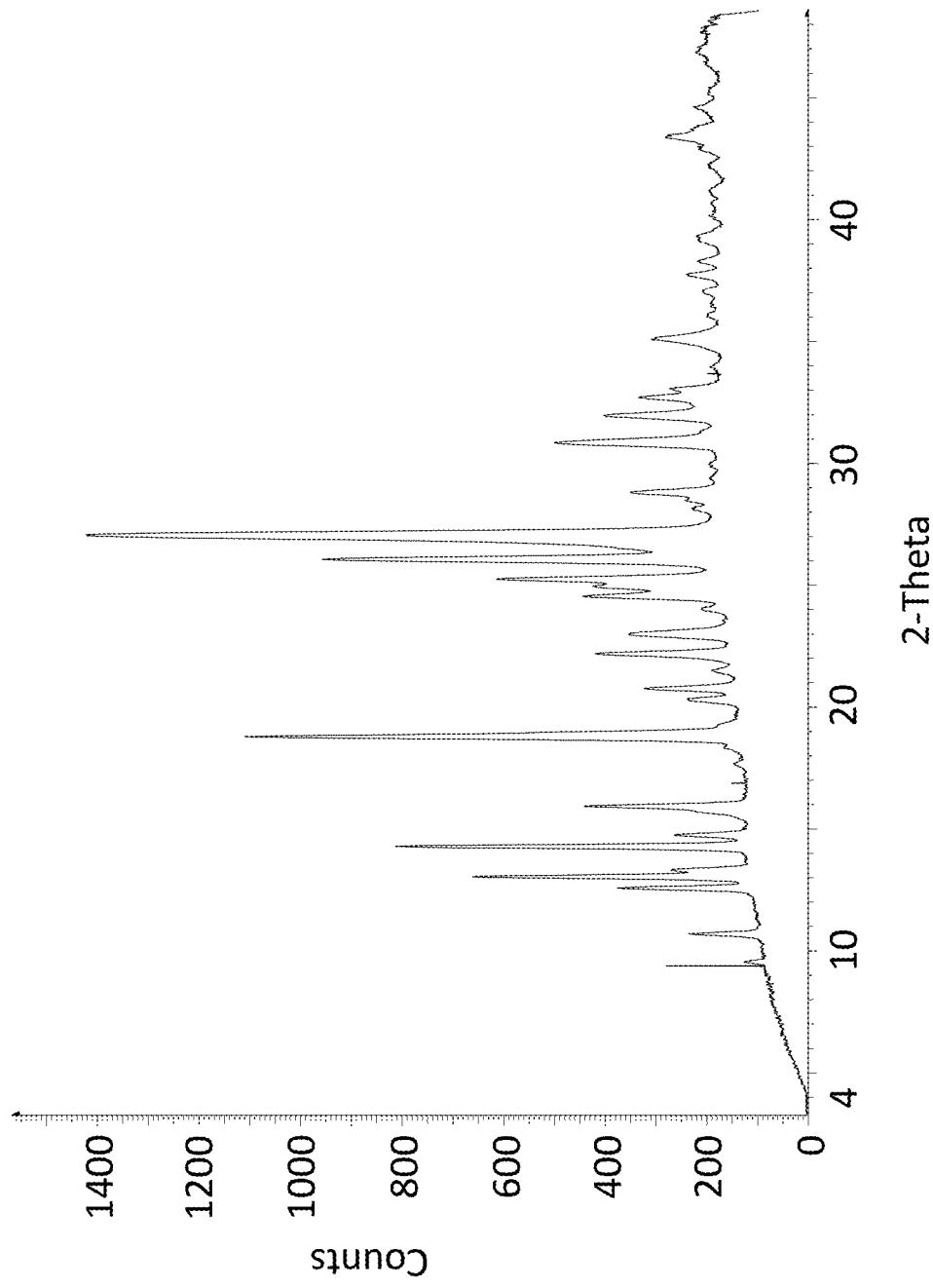
FIG. 1 - Representative X-ray powder diffraction pattern of Form A (anhydrous form)

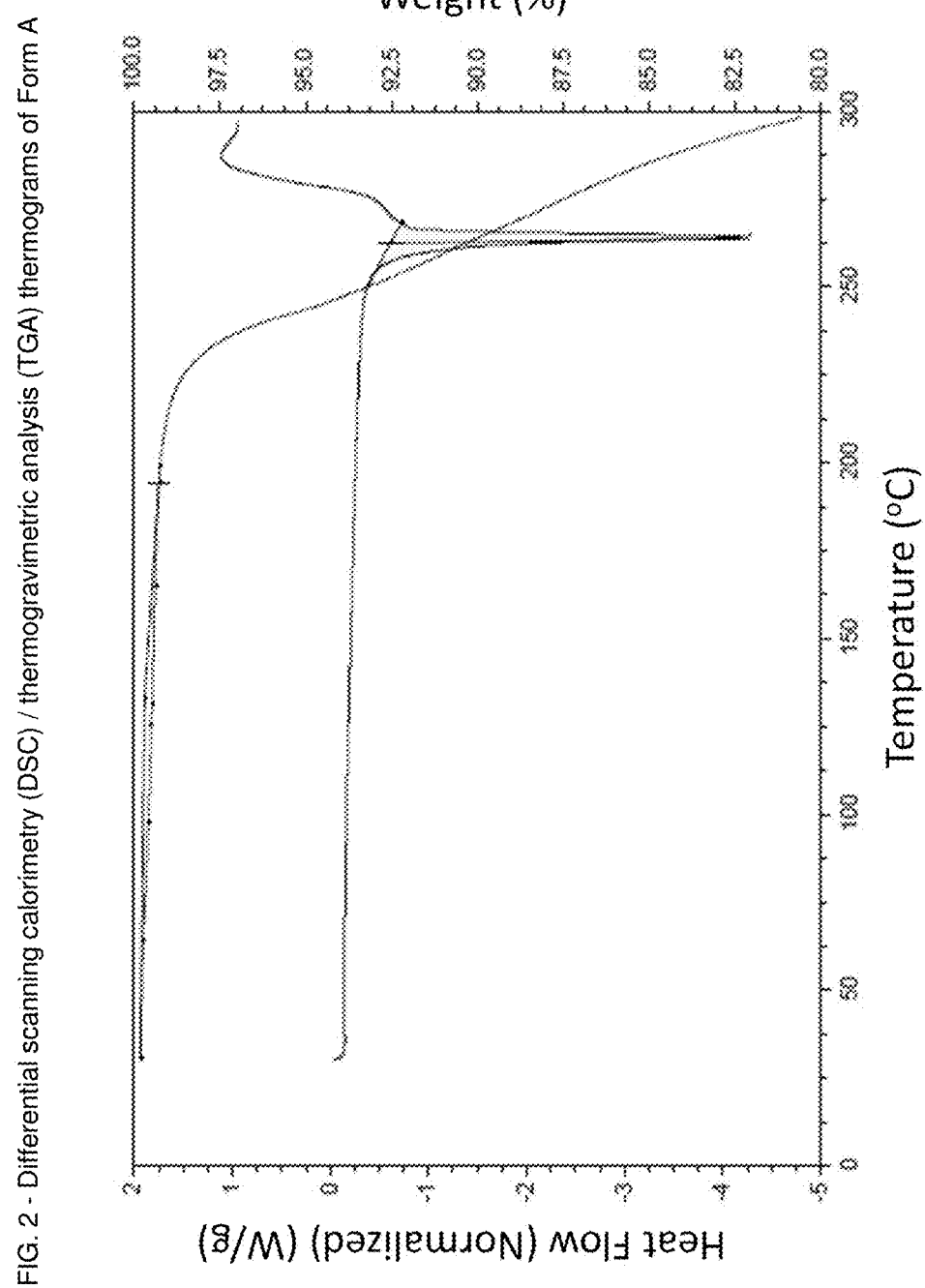
FIG. 2 - Differential scanning calorimetry (DSC) / thermogravimetric analysis (TGA) thermograms of Form A

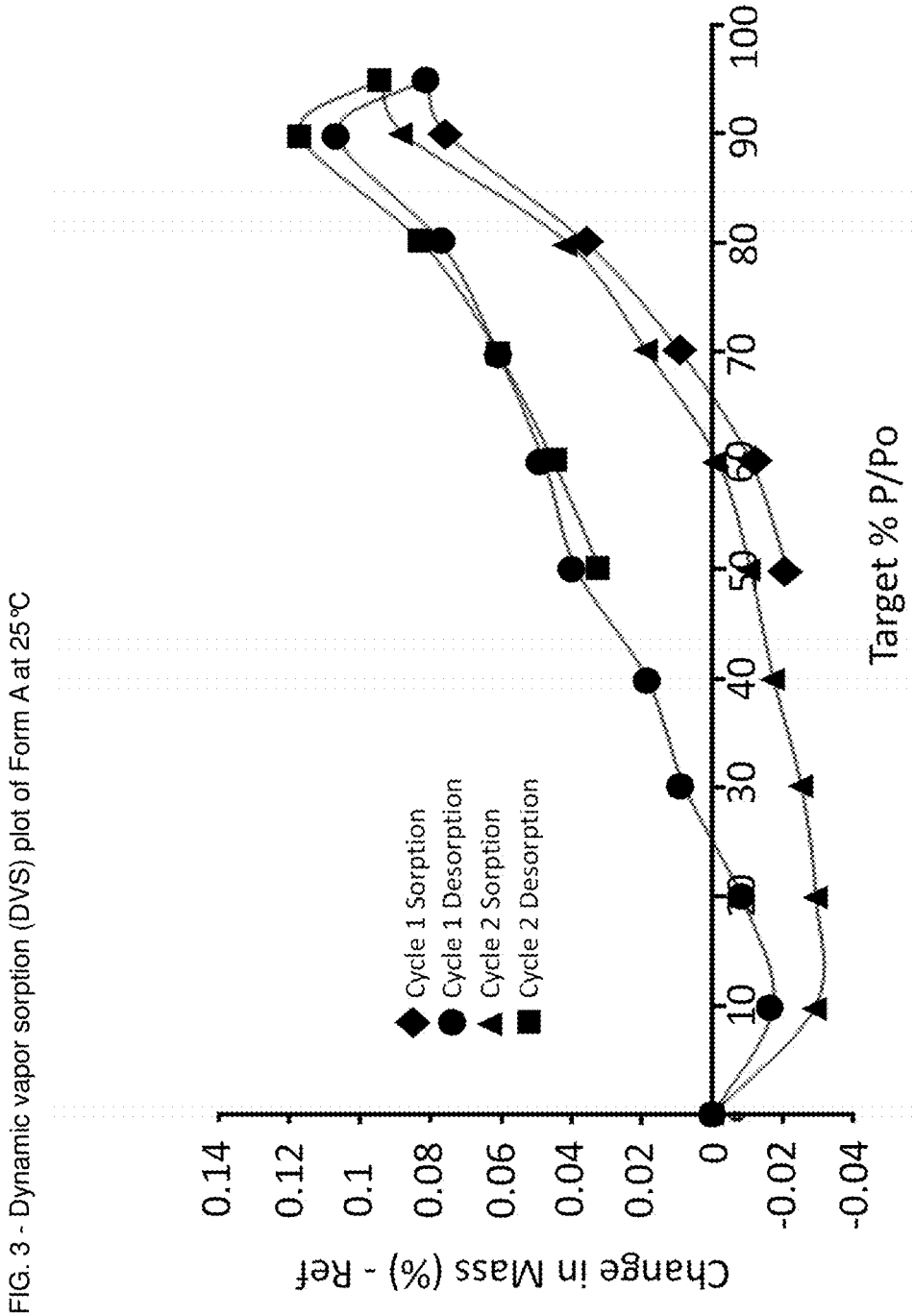
FIG. 3 - Dynamic vapor sorption (DVS) plot of Form A at 25 °C

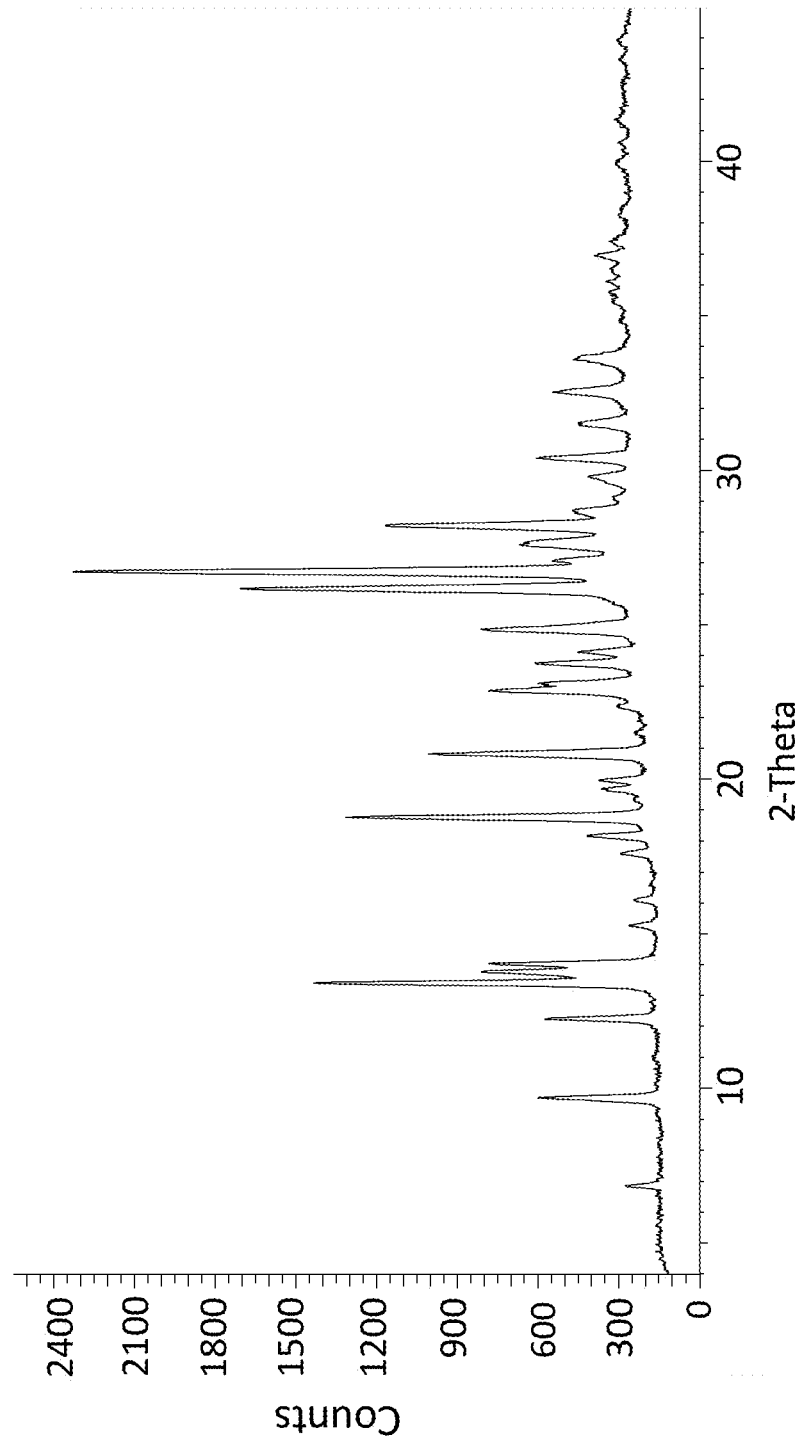
FIG. 4 - Representative X-ray powder diffraction pattern of Form $H_A$ (monohydrate form)

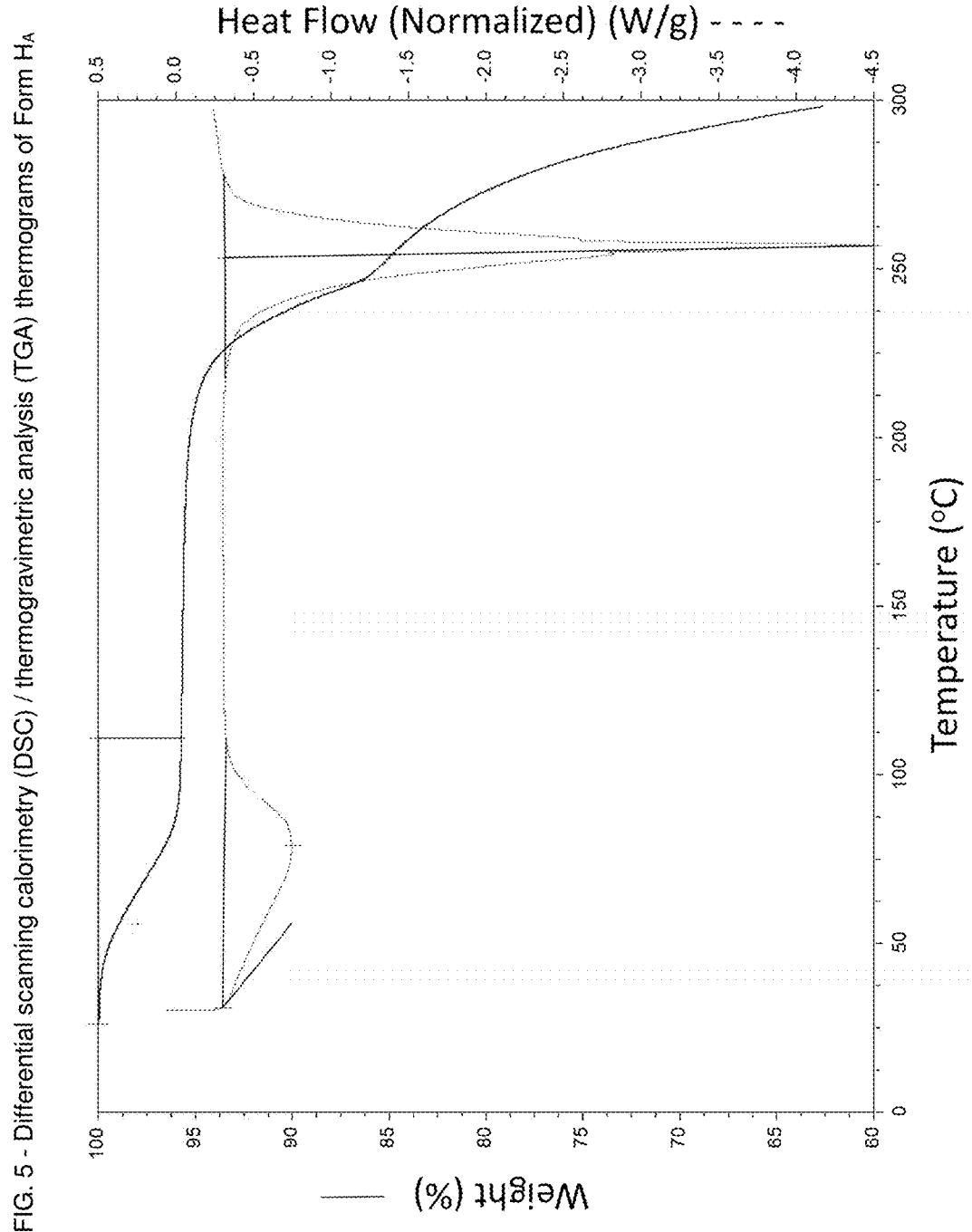
FIG. 5 - Differential scanning calorimetry (DSC) / thermogravimetric analysis (TGA) thermograms of Form $H_A$

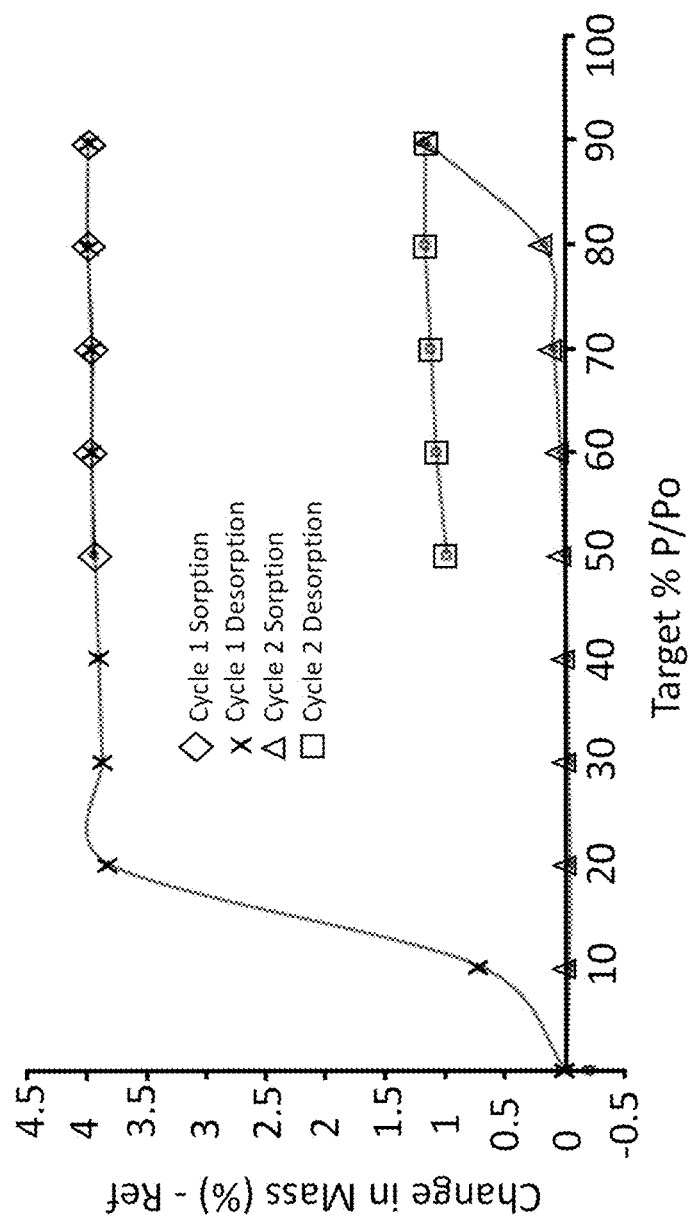
FIG. 6 - Dynamic vapor sorption plot of Form H$_A$ at 25 °C

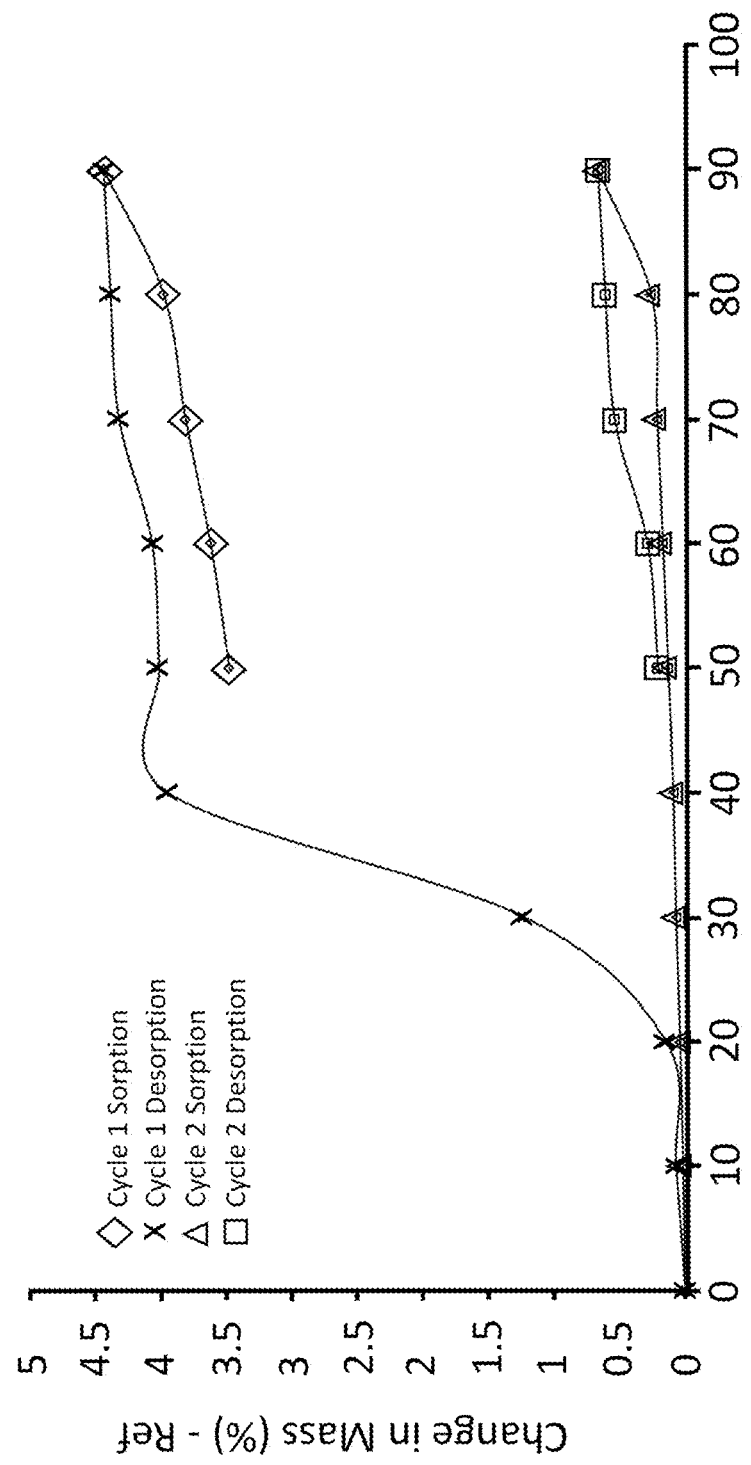
FIG. 7 - Dynamic vapor sorption plot of Form H$_A$ at 50 °C

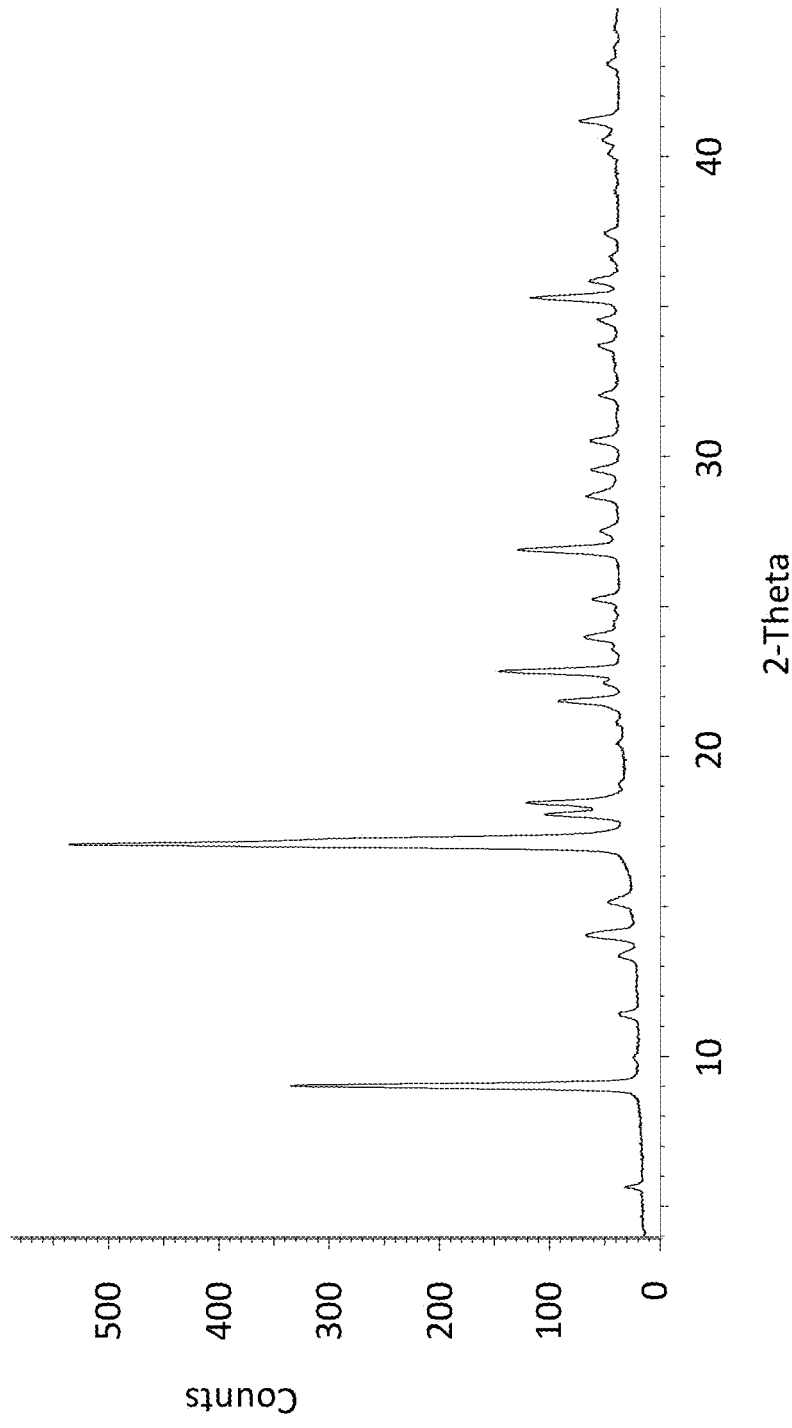
FIG. 8 - Representative X-ray powder diffraction pattern of Form $H_B$ (dihydrate form)

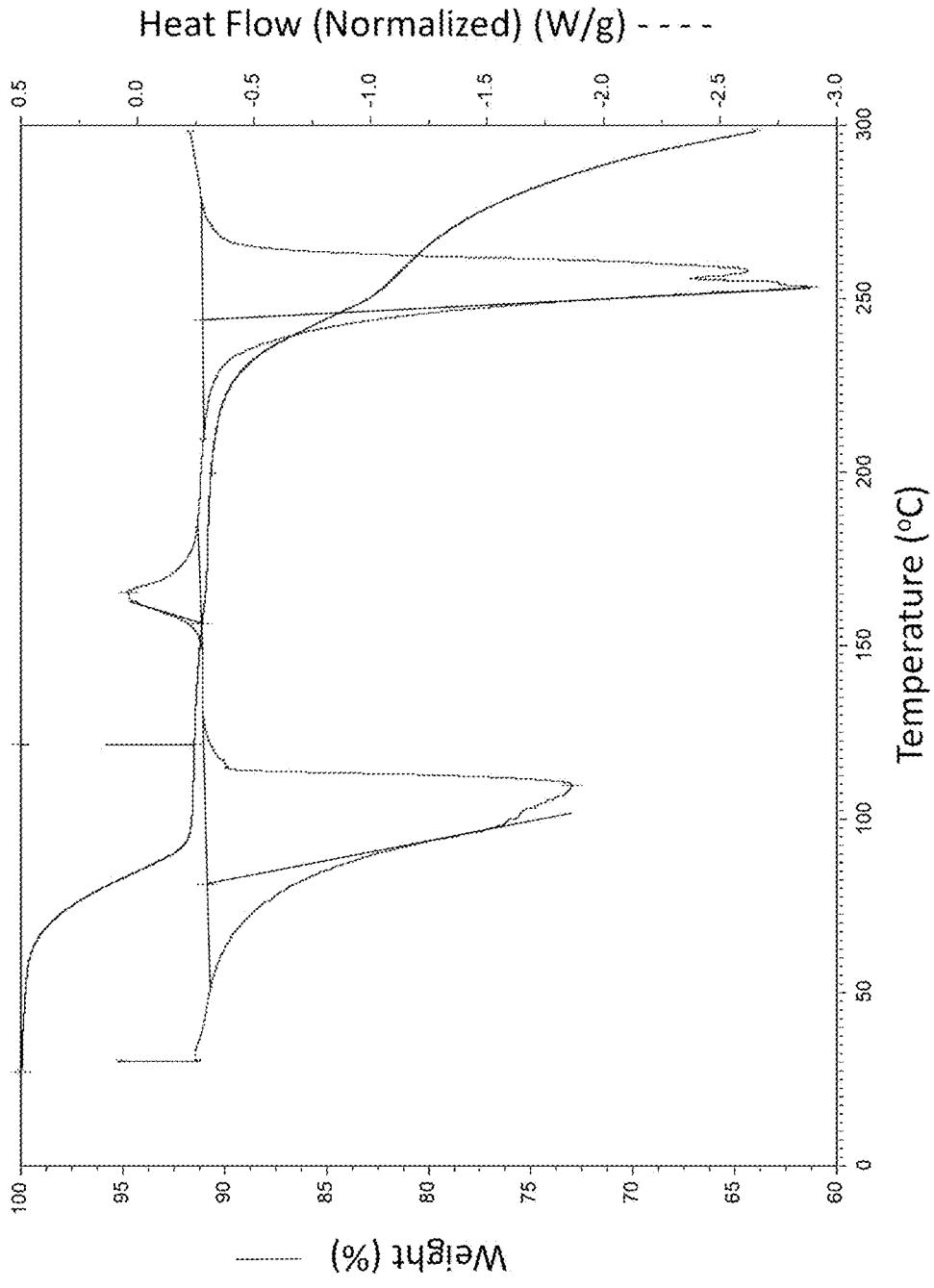
FIG. 9 - Differential scanning calorimetry (DSC) / thermogravimetric analysis (TGA) thermograms of Form $H_B$

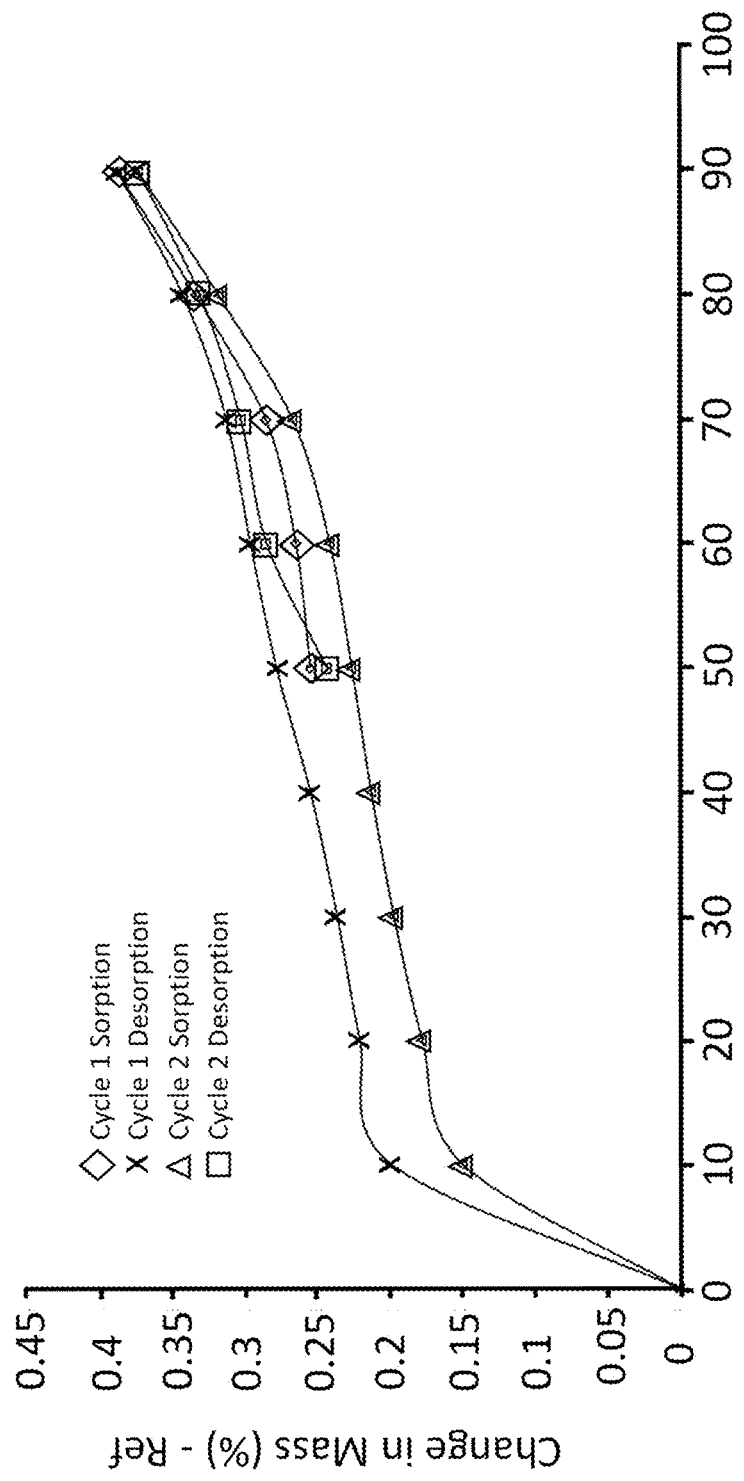
FIG. 10 - Dynamic vapor sorption plot of Form $H_B$ at 25°C

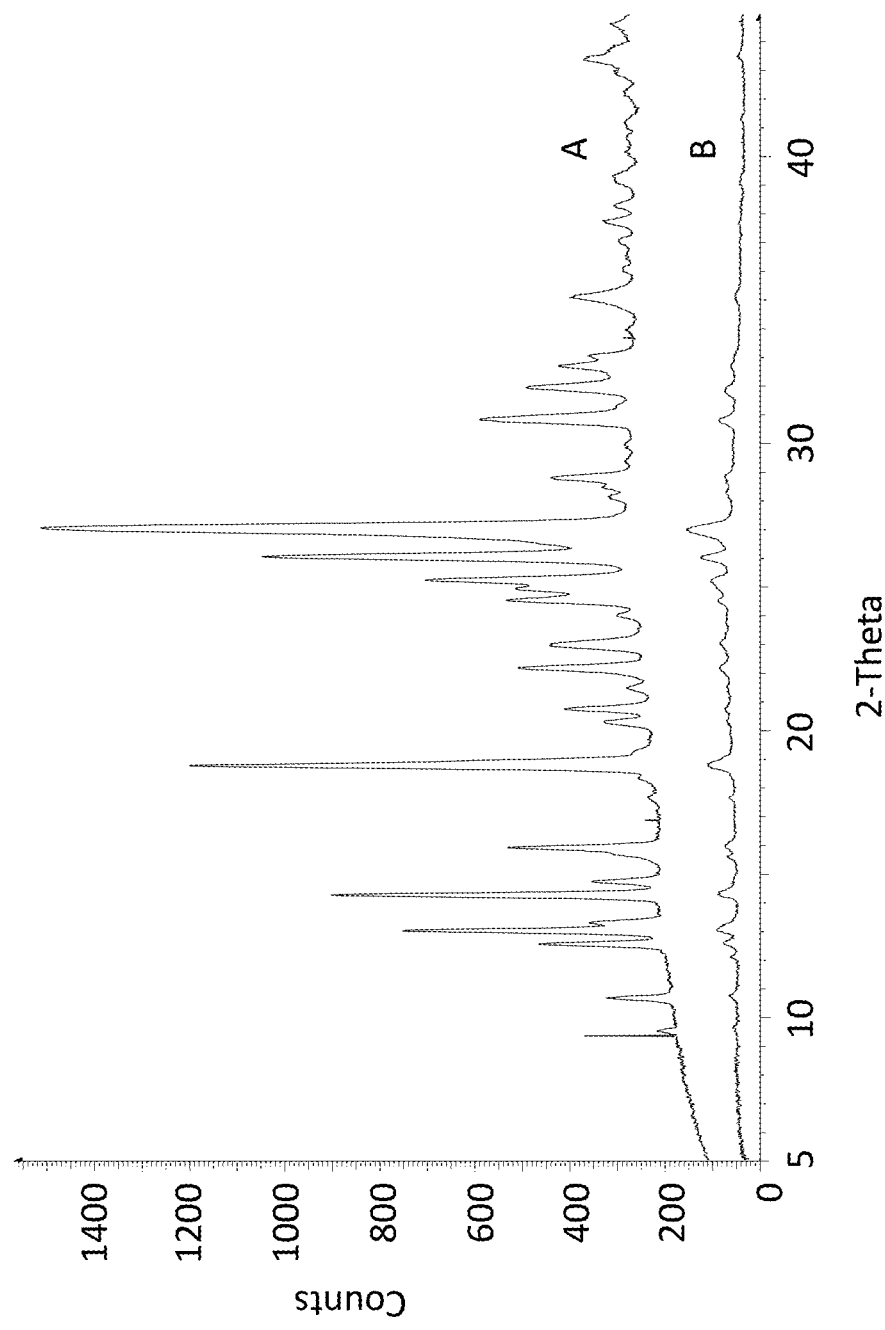
FIG. 11 - Comparison of Form A obtained by the procedure (A) described in Example 3 vs. obtained by the procedure (B) described in Example 2 (also described in US 14/977,273)

CRYSTALLINE FORMS OF A TRIAZOLOPYRIMIDINE COMPOUND

CROSS-REFERENCE TO RELATED APPLICATIONS

This application is a divisional of U.S. Ser. No. 16/311,638, filed Dec. 19, 2018, which is the U.S. National Stage of International Application No. PCT/CN2017/089003, filed Jun. 19, 2017, which claims the benefit of priority to International Application Patent Application No. PCT/CN2016/086350, filed Jun. 20, 2016, the contents of which are incorporated herein by reference.

FIELD OF THE INVENTION

This invention relates to crystalline forms of N-((5-Fluoro-2,3-dihydrobenzofuran-4-yl)methyl)-8-(2-methylpyridin-3-yl)-[1,2,4]triazolo[4,3-c]pyrimidin-5-amine hydrochloride, pharmaceutical compositions comprising the same, and methods of treatment using the crystalline forms and processes for preparing the crystalline forms.

BACKGROUND

Polycomb group (PcG) proteins are chromatin modifying enzymes that are dysregulated in many human cancers. The Polycomb Repressive Complex 2 (PRC2), which includes SUZ12 (suppressor of zeste 12), EED (embryonic ectoderm development) and the catalytic subunit, EZH2 (enhancer of zeste homolog 2), represses genes by methylating the core histone H3 lysine 27 (H3K27me3) at and around the promoter regions of target genes. PRC2 is the critical component of cellular machinery involved in the epigenetic regulation of gene transcription and plays critical function in development and tissue differentiation and regeneration. Although EZH2 is the catalytic subunit, PRC2 requires at least EED and SUZ12 for its methyltransferase activity. EED, SUZ12 and EZH2 are overexpressed in many cancers, including but not limited to breast cancer, prostate cancer, hepatocellular carcinoma and etc. EZH2 activating mutations have been identified in DLBCL (diffused large B cell lymphoma) patients and FL (follicular lymphoma) patients. Inhibition of PRC2 methyltransferase activity by compounds competing with the cofactor S-adenosyl methionine (SAM) in DLBCL reverses H3K27 methylation, re-activates expression of target genes and inhibits tumor growth/proliferation. Therefore, PRC2 provides a pharmacological target for DLBCL and other cancers.

In preparing a pharmaceutical composition, a form of the therapeutic agent is sought that has a balance of desired properties, such as, for example, dissolution rate, solubility, bioavailability, and/or storage stability. The existence of multiple solid forms, often referred to as polymorphs, is well known for solid pharmaceutical compounds, and the chemical and physical stability as well as handling properties of such compounds often depend on which solid form is used. Accordingly, the selection of a particular solid form of the active drug substance (e.g., a salt form, hydrated or solvated form, or polymorphic form) is often very important in the design of a reliable and reproducible production process, and in storage, handling and distribution of a safe and effective form of the drug substance.

"Impurities: Guideline for Residual Solvents", is a guideline on amounts of residual solvents tolerated in pharmaceuticals, which was produced by the the International Council for Harmonisation of of Technical Requirements for Pharmaceuticals for Human Use (ICH). This Guideline recommends the use of less toxic solvents in the manufacture of drug substances and dosage forms, and sets pharmaceutical limits for residual solvents (organic volatile impurities) in drug products. This guidance divides solvents into three risk-based classes: Class 1 solvents, which are known to cause unacceptable toxicities; Class 2 solvents, which are associated with less severe toxicity; and Class 3 solvents, which have low toxic potential.

According to the ICH Guidance, residual amounts of Class 3 solvents of 50 mg per day or less (corresponding to 5000 ppm or 0.5%) would be acceptable without justification. The concentration limits are calculated using the equation below by assuming a product mass of 10 g administered daily:

Concentration (ppm)=(1000×PDE)/dose

PDE (permitted daily exposure) is given in terms of mg/day and dose is given in g/day. Higher amounts of Class 3 solvents may also be acceptable provided they are realistic in relation to manufacturing capability and good manufacturing practice.

Patent application number U.S. Ser. No. 14/977,273, which is herein incorporated by reference, discloses certain triazolopyrimidine compounds for treating PRC2-mediated diseases or disorders. This patent application was published on 23 Jun. 2016 as US 2016-0176882. One compound disclosed in that application is N-((5-Fluoro-2,3-dihydrobenzofuran-4-yl)methyl)-8-(2-methylpyridin-3-yl)-[1,2,4]triazolo[4,3-c]pyrimidin-5-amine (free form) and its hydrochloride salt. The free form (referred to herein as Compound A) has the following structure:

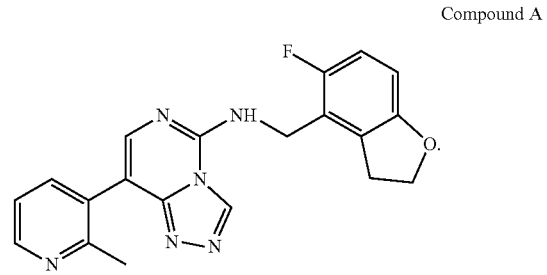 [SMILES: Cc1ncccc1-c1cnc(NCc2c(F)ccc3c2CCO3)n2cnnc12]

Compound A

The hydrochloride salt (referred to herein as Compound X) has the following structure:

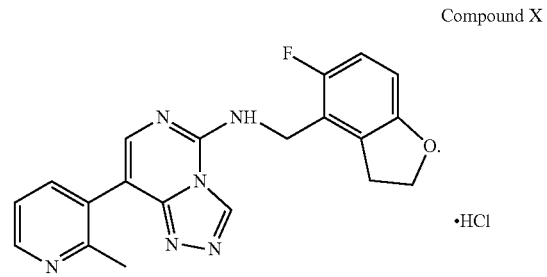 [SMILES: Cc1ncccc1-c1cnc(NCc2c(F)ccc3c2CCO3)n2cnnc12 ; Cl]

Compound X

The free form, Compound A, displays low aqueous solubilities both at physiologically relevant pH level of 7.4 and in simulated gastric fluid (SGF). It was found that exposures of Compound A were under-proportional at higher doses in rodent pharmacokinetic studies, which may lead to insufficient and variable exposures in clinical settings. Experiments were carried out to find an appropriate salt to improve aqueous solubility. It was discovered that only the hydrochloric salt provides the necessary improvement in solubility, and demonstrates the dose-proportional exposure in rodent after testing a number of salts that also included phosphate, fumarate, tartarate, succinate, maleate and mesylate.

The procedure described in U.S. Ser. No. 14/977,273 to produce Compound X uses isopropanol (IPA, a Class 3 solvent) as the medium. Variable amounts of IPA were observed in different batches of Compound X obtained by the procedure described in U.S. Ser. No. 14/977,273 as determined by $^1$H NMR (exemplified by entry 1 in table 2 below), with the amount of IPA in some batches being more than 0.5% by weight. It has also been very difficult to remove the residual IPA from the final product. Additionally, Compound X thus obtained showed low and variable crystallinities, as judged from the XRPD spectra. Efforts were made to remove the residual IPA and improve crystallinality without much success. Therefore, the need exists for methods that can consistently produce Compound X in the desired form, i.e., a form that is substantially free of residual organic solvent and which shows improved and reliable crystallinity.

SUMMARY

The present invention provides crystalline forms of Compound X (N-((5-Fluoro-2,3-dihydrobenzofuran-4-yl)methyl)-8-(2-methylpyridin-3-yl)-[1,2,4]triazolo[4,3-c]pyrimidin-5-amine hydrochloride).

Embodiments of these crystalline forms include those characterized herein as Forms A, $H_A$ and $H_B$ as well as combinations or mixtures of these crystalline forms.

TABLE 1

| Compound X | Form |
| --- | --- |
| Anhydrous | A |
| monohydrate | $H_A$ |
| dihydrate | $H_B$ |

The names used herein to characterize a specific form, e.g. "$H_A$" etc., should not be considered limiting with respect to any other substance possessing similar or identical physical and chemical characteristics, but rather it should be understood that these designations are mere identifiers that should be interpreted according to the characterization information also presented herein.

The present invention provides methods of preparation of crystalline forms of Compound X.

The present invention also provides pharmaceutical compositions comprising crystalline form(s) of Compound X and at least one pharmaceutically acceptable carrier, diluent or excipient. The pharmaceutical composition may further comprise at least one additional therapeutic agent. Of particular interest are additional therapeutic agents selected from: other anti-cancer agents, immunomodulators, anti-allergic agents, anti-nausea agents (or anti-emetics), pain relievers, cytoprotective agents, and combinations thereof.

Crystalline form(s) of Compound X of the present invention may be used in the treatment of diseases or disorders mediated by EED and/or PRC2.

Crystalline form(s) of Compound X of the present invention may be used in therapy.

Crystalline form(s) of Compound X of the present invention may be used for the manufacture of a medicament for the treatment of diseases or disorders mediated by EED and/or PRC2.

Other features and advantages of the present disclosure will be apparent from the following detailed description and claims.

BRIEF DESCRIPTION OF THE DRAWINGS

FIG. 1 depicts a representative X-ray powder diffraction pattern of Form A (anhydrous form).

FIG. 2 depicts differential scanning calorimetry (DSC)/thermogravimetric analysis (TGA) thermograms of Form A.

FIG. 3 depicts a dynamic vapor sorption (DVS) plot of Form A at 25° C.

FIG. 4 depicts a representative X-ray powder diffraction pattern of Form $H_A$ (monohydrate form).

FIG. 5 depicts differential scanning calorimetry (DSC)/thermogravimetric analysis (TGA) thermograms of Form $H_A$.

FIG. 6 depicts a dynamic vapor sorption plot of Form $H_A$ at 25° C.

FIG. 7 depicts a dynamic vapor sorption plot of Form $H_A$ at 50° C.

FIG. 8 depicts a representative X-ray powder diffraction pattern of Form $H_B$ (dihydrate form).

FIG. 9 depicts differential scanning calorimetry (DSC)/thermogravimetric analysis (TGA) thermograms of Form $H_B$.

FIG. 10 depicts a dynamic vapor sorption plot of Form $H_B$ at 25° C.

FIG. 11 depicts comparison of Form A obtained by the procedure (A) described in Example 3 below vs. obtained by the procedure (B) described in Example 2 below (also described in U.S. Ser. No. 14/977,273).

DETAILED DESCRIPTION

The following enumerated embodiments of the invention are representative:

1. Crystalline Form A of N-((5-Fluoro-2,3-dihydrobenzofuran-4-yl)methyl)-8-(2-methylpyridin-3-yl)-[1,2,4]triazolo[4,3-c]pyrimidin-5-amine hydrochloride, wherein said Form A contains less than 0.5% by weight of residual organic solvent.
2. Crystalline Form A of N-((5-Fluoro-2,3-dihydrobenzofuran-4-yl)methyl)-8-(2-methylpyridin-3-yl)-[1,2,4]triazolo[4,3-c]pyrimidin-5-amine hydrochloride, wherein said Form A contains less than 0.2% by weight of residual organic solvent.
3. Crystalline Form A of N-((5-Fluoro-2,3-dihydrobenzofuran-4-yl)methyl)-8-(2-methylpyridin-3-yl)-[1,2,4]triazolo[4,3-c]pyrimidin-5-amine hydrochloride, wherein said Form A contains less than 0.1% by weight of residual organic solvent.
4. Crystalline Form A of Compound X obtained by a process comprising the steps:
   1) suspending N-((5-Fluoro-2,3-dihydrobenzofuran-4-yl)methyl)-8-(2-methylpyridin-3-yl)-[1,2,4]triazolo[4,3-c]pyrimidin-5-amine (Compound A) in a mixture of water and water-miscible organic solvent;
   2) heating the resulting suspension to about or over 50° C.;
   3) acidifying the resulting suspension to form a clear solution while maintaining the temperature at about or over 50° C.; and 4) lowering the temperature of the resulting solution to to obtain Form A of Compound X.
5. Crystalline Form A of Compound X of any one of embodiments 1 to 3, obtained by a process comprising the steps:
   1) suspending N-((5-Fluoro-2,3-dihydrobenzofuran-4-yl) methyl)-8-(2-methylpyridin-3-yl)-[1,2,4]triazolo[4,3-c]pyrimidin-5-amine (Compound A) in a mixture of water and water-miscible organic solvent;
   2) heating the resulting suspension to about or over 50° C.;
   3) acidifying the resulting suspension to form a clear solution while maintaining the temperature at about or over 50° C.; and
   4) lowering the temperature of the resulting solution to to obtain Form A of Compound X.
6. Crystalline Form A of Compound X of embodiment 5, obtained by a process wherein:
   in step 1) the water-miscible organic solvent is selected from a group consisting of ethanol and acetone;
   in step 2) heating the resulting suspension to about 50 to 75° C.;
   in step 3) acidifying the resulting suspension to form a clear solution by adding a solution of 0.5 N HCl in a mixture of water and said water-miscible organic solvent, while maintaining the temperature at about 50 to 75° C.; and
   in step 4) lowering the temperature of the resulting solution to to obtain Form A of Compound X.
7. A hydrated solid form of N-((5-Fluoro-2,3-dihydrobenzofuran-4-yl)methyl)-8-(2-methylpyridin-3-yl)-[1,2,4]triazolo[4,3-c]pyrimidin-5-amine hydrochloride.
8. The hydrated solid form according to embodiment 7, wherein said hydrated form is monohydrate Form $H_A$.
9. The hydrated solid form according to embodiment 7, wherein said hydrated form is dihydrate Form $H_B$.
10. A crystalline form of N-((5-Fluoro-2,3-dihydrobenzofuran-4-yl)methyl)-8-(2-methylpyridin-3-yl)-[1,2,4]triazolo[4,3-c]pyrimidin-5-amine hydrochloride (Form $H_A$) having a X-ray powder diffraction pattern comprising the following 2θ values (CuKα λ=1.5418 Å): 13.8±0.1, 20.8±0.1, 26.2±0.1, 26.7±0.1, and 28.2±0.1. In some embodiments, Form $H_A$ has one or more (e.g., 2, 3, 4 or 5) additional 2θ values selected from those in List 2.
11. A crystalline form of N-((5-Fluoro-2,3-dihydrobenzofuran-4-yl)methyl)-8-(2-methylpyridin-3-yl)-[1,2,4]triazolo[4,3-c]pyrimidin-5-amine hydrochloride (Form $H_B$) having a X-ray powder diffraction pattern comprising the following 2θ values (CuKα λ=1.5418 Å): 9.0±0.1, 17.1±0.1, 22.8±0.1, 26.9±0.1, and 35.3±0.1. In some embodiments, Form $H_B$ has one or more (e.g., 2, 3, 4 or 5) additional 2θ values selected from those in List 3.
12. A pharmaceutical composition, comprising one or more pharmaceutically acceptable carriers and Form A described in any one of embodiments 1 to 6.
13. The pharmaceutical composition of embodiment 12 further comprising at least one additional therapeutic agent.
14. The pharmaceutical composition of embodiment 13 where said additional therapeutic agent is selected from other anti-cancer agents, immunomodulators, anti-allergic agents, anti-emetics, pain relievers, cytoprotective agents, and combinations thereof.
15. Crystalline Form A described in any one of embodiments 1 to 6 for use in therapy.
16. Use of Form A described in any one of embodiments 1 to 6, in the manufacture of a medicament for treating a disease or disorder mediated by EED and/or PRC2.
17. The use of embodiment 16, wherein said disease or disorder is selected from diffused large B cell lymphoma, follicular lymphoma, other lymphomas, leukemia, multiple myeloma, mesothelioma, gastric cancer, malignant rhabdoid tumor, hepatocellular carcinoma, prostate cancer, breast carcinoma, bile duct and gallbladder cancers, bladder carcinoma, brain tumors including neuroblastoma, schwannoma, glioma, glioblastoma and astrocytoma, cervical cancer, colon cancer, melanoma, endometrial cancer, esophageal cancer, head and neck cancer, lung cancer, nasopharyngeal carcinoma, ovarian cancer, pancreatic cancer, renal cell carcinoma, rectal cancer, thyroid cancers, parathyroid tumors, uterine tumors, and soft tissue sarcomas.
18. A process for preparing Crystalline Form A of Compound X comprising the steps:
   1) suspending N-((5-Fluoro-2,3-dihydrobenzofuran-4-yl) methyl)-8-(2-methylpyridin-3-yl)-[1,2,4]triazolo[4,3-c]pyrimidin-5-amine (Compound A) in a mixture of water and water-miscible organic solvent;
   2) heating the resulting suspension to about or over 50° C.;
   3) acidifying the resulting suspension to form a clear solution while maintaining the temperature at about or over 50° C.; and
   4) lowering the temperature of the resulting solution to obtain Form A of Compound X.
19. A process for preparing Crystalline Form A of Compound X that contains less than 0.5% by weight of residual organic solvent, preferably less than 0.3% weight of residual organic solvent, more preferably less than 0.1% weight of residual organic solvent, comprising the steps:
   1) suspending N-((5-Fluoro-2,3-dihydrobenzofuran-4-yl) methyl)-8-(2-methylpyridin-3-yl)-[1,2,4]triazolo[4,3-c]pyrimidin-5-amine (Compound A) in a mixture of water and water-miscible organic solvent;
   2) heating the resulting suspension to about or over 50° C.;
   3) acidifying the resulting suspension to form a clear solution while maintaining the temperature at about or over 50° C.; and
   4) lowering the temperature of the resulting solution to prompt formation of crystals to obtain Form A of Compound X.
20. The process of embodiment 19 wherein:
   in step 1) the water-miscible organic solvent is selected from a group consisting of ethanol and acetone;
   in step 2) heating the resulting suspension to about 50 to 75° C.;
   in step 3) acidifying the resulting suspension to form a clear solution by adding a solution of 0.5 N HCl in a mixture of water and said water-miscible organic solvent, while maintaining the temperature at about 50 to 75° C.; and in step 4) lowering the temperature of the resulting solution to obtain Form A of Compound X.

It was postulated that IPA may be trapped in the crystalline lattice when Compound X is formed in a médium of isopropanol, since during the entire salt formation process the material remained as a "slurry" and was never fully dissolved. Table 2 summarizes the results obtained from the experiments carried out with selected Class 3 solvents and combinations thereof. It was unexpectedly discovered that EtOH/water and acetone/water (Entries 11 and 12) enabled complete dissolution of Compound X and also sustained the supersaturation state for optimal duration, especially at elevated temperature. These combinations provide crystalline forms of Compound X that are substantially free of organic solvents, e.g. containing not more than 0.3% and typically not more than 0.1% organic solvent by weight after normal drying.

TABLE 2

| No. | Solvent | Compound A solubility (mg/mL) | | Compound X solubility (mg/mL) | |
|---|---|---|---|---|---|
| | | 50° C. | rt | 50° C. | rt |
| 1 | Acetone | <10 | <10 | <10 | <10 |
| 2 | ACN | <10 | <10 | <10 | <10 |
| 3 | IPA | <10 | <10 | <10 | <10 |
| 4 | MeOH | <10 | <10 | >10 | >10 |
| 5 | EtOH | <10 | <10 | <10 | <10 |
| 6 | EtOAc | <10 | <10 | <10 | <10 |
| 7 | THF | <10 | <10 | <10 | <10 |
| 8 | MTBE | <10 | <10 | <10 | <10 |
| 9 | Heptane | <10 | <10 | <10 | <10 |
| 10 | Water | <10 | <10 | <10 | <10 |
| 11 | EtOH/H$_2$O (1/1) | <10 | <10 | >50 | <50 |
| 12 | Acetone/H$_2$O (1/1) | <10 | <10 | >50 | <50 |

With the selected solvent pair, the crystallization conditions were further optimized, as listed in Table 3. The conditions as shown in Entries 5 and 6 in Table 3 were found to produce the material with much lower content of the residual organic solvent and higher crystallinity, while better yield was obtained with the conditions in Entry 5. The conditions of Entry 5 could also be reproduced in multi-gram scale, as indicated as Entry 7 in Table 3.

Form A of Compound X (Anhydrous Form)

In one embodiment, Compound X is provided as a crystalline material comprising Form A. The crystalline form of Compound X comprises a crystalline form referred to herein as "Form A" of Compound X.

In one embodiment, Form A of Compound X is characterized by unit cell parameters approximately equal to the following:

| Unit cell dimensions: | a = 8.468(5) Å | α = 102.58(2)° |
|---|---|---|
| | b = 9.615(5) Å | β = 92.45(3)° |
| | c = 12.102(7) Å | γ = 99.26(3)° |

Space group: P-1
Molecules of Compound X/asymmetric unit: 2

Volume/Number of molecules in the unit cell=946.0 (9) Å$^3$

Density (calculated)=1.449 g/cm$^3$ wherein the unit cell parameters of Form A of Compound X are measured at a temperature of about 100(±2) K (−173° C.).

In one embodiment, the invention provides Form A of Compound X which characterized by an X-ray powder diffraction pattern comprising the following 2θ values (CuKα λ=1.5418 Å): 12.5±0.1, 13.0±0.1, 25.2±0.1, and 30.8±0.1. In another embodiment, in addition to the above specified 2θ values, Form A exhibits one or more (e.g., 2, 3, 4 or 5) additional 2θ values selected from those in List 1. In yet another embodiment, Form A exhibits an X-ray powder diffraction pattern substantially the same as that shown in FIG. 1.

List 1: XRPD peak listing for Form A of Compound X (2θ: most intense peaks are underlined)

Angle °2θ

7.3
9.5
10.6
12.5
<u>13.0</u>
<u>14.2</u>
14.7
15.8
<u>18.7</u>
20.2
20.7

TABLE 3

| | | | Conditions | | | | Amount of | | |
|---|---|---|---|---|---|---|---|---|---|
| Entry | Amount | Temp. | Solvent, amount | Solvent multiples (fold) | Appreparance | Solvent residue | Solvent residue* (%) | Crystallinity | Yield (%) |
| 1 | 6 g | 50° C. | IPA, 90 mL | 15× | slurry | IPA | 0.80 | Low | 98% |
| 2 | 0.100 g | 75° C. | EtOH, 5 mL | 50× | homogenous | EtOH | 0.80 | Medium | 79.3 |
| 3 | 0.050 g | 75° C. | EtOH, 4 mL | 80× | homogenous | EtOH | 0.36 | High | 59.6 |
| 4 | 0.050 g | 75° C. | EtOH, 5 mL | 100× | homogenous | EtOH | 0.24 | High | 55.2 |
| 5 | 0.100 g | 75° C. | 95% EtOH/H$_2$O, 5 mL | 50× | homogenous | EtOH | 0.16 | High | 67.6 |
| 6 | 0.100 g | 75° C. | 90% EtOH/H$_2$O, 5 mL | 50× | homogenous | EtOH | 0.08 | High | 54.9 |
| 7 | 4 g | 75° C. | 95% EtOH/H$_2$O, 200 mL | 50× | homogenous | EtOH | 0.04 | High | 79.7 |

*The amount of the solvent residue was determined by $^1$HNMR

-continued

List 1: XRPD peak listing for Form A of Compound
X (2θ: most intense peaks are underlined)

| Angle °2θ |
|---|
| 22.1 |
| 22.9 |
| 24.5 |
| 25.2 |
| 26.0 |
| 26.9 |
| 28.7 |
| 30.8 |
| 31.9 |
| 32.6 |
| 35.1 |

In another embodiment, Form A of Compound X exhibits a strong endotherm during DSC at about 264±1° C.

In another embodiment, Form A of Compound X has gradual loss of mass via TGA amounting to about 0.6% loss by 200° C.

Form $H_A$ of Compound X (Monohydrate)

In one embodiment, Compound X is provided as a monohydrate in a crystalline form referred to herein as "Form $H_A$" of Compound X. Form $H_A$ of Compound X has a stoichiometry of one molecule of water for each molecule of Compound X.

In one aspect, the invention provides Form $H_A$ of Compound X which characterized by an X-ray powder diffraction pattern comprising the following 2θ values (CuKα λ=1.5418 Å): 13.8±0.1, 20.8±0.1, 26.2±0.1, 26.7±0.1, and 28.2±0.1. In another embodiment, in addition to the above specified 2θ values, Form $H_A$ exhibits one or more (e.g., 2, 3, 4 or 5) additional 2θ values selected from those in List 2. In yet another embodiment, Form $H_A$ exhibits an X-ray powder diffraction pattern substantially the same as that shown in FIG. 4.

LIST 2: XRPD peak listing for Form $H_A$ of Compound
X (2θ: most intense peaks are underlined)

| Angle °2θ |
|---|
| 9.7 |
| 12.3 |
| <u>13.4</u> |
| 13.8 |
| 14.0 |
| 18.2 |
| <u>18.9</u> |
| 20.8 |
| 22.9 |
| 23.1 |
| 23.8 |
| 24.9 |
| <u>26.2</u> |
| <u>26.7</u> |
| 27.1 |
| 27.6 |
| 27.7 |
| 28.2 |
| 30.4 |
| 32.5 |

It has been discovered that monohydrate is easily formed in water/solvent mixtures with water activity above 0.5~0.6 and it shows acceptable stability to humidity and temperature.

In another embodiment, Form $H_A$ of Compound X exhibits a strong endotherm during DSC at about 256±1° C.

In another embodiment, Form $H_A$ of Compound X has gradual loss of mass via TGA amounting to about 4.2% loss by 111° C.

Form $H_B$ of Compound X (Dihydrate)

In one embodiment, Compound X is provided as a dihydrate in a crystalline form referred to herein as "Form $H_B$" of Compound X. Form $H_B$ of Compound X has a stoichiometry of two molecules of water for each molecule of Compound X.

In one aspect, the invention provides Form $H_B$ of Compound X which characterized by an X-ray powder diffraction pattern comprising the following 2θ values (CuKα λ=1.5418 Å): 9.0±0.1, 17.1±0.1, 22.8±0.1, 26.9±0.1, and 35.3±0.1. In another embodiment, in addition to the above specified 2θ values, Form $H_B$ exhibits one or more (e.g., 2, 3, 4 or 5) additional 2θ values selected from those in List 3. In yet another embodiment, Form $H_B$ exhibits an X-ray powder diffraction pattern substantially the same as that shown in FIG. 8.

List 3: XRPD peak listing for Form $H_B$ of Compound
X (2θ: most intense peaks are underlined)

| Angle °2θ |
|---|
| <u>9.0</u> |
| 14.0 |
| <u>17.1</u> |
| 18.1 |
| 18.5 |
| 21.9 |
| 22.8 |
| 24.0 |
| 25.2 |
| 26.9 |
| 28.7 |
| 29.6 |
| 30.5 |
| 35.3 |
| 35.9 |
| 41.2 |

In another embodiment, Form $H_B$ of Compound X exhibits a strong endotherm during DSC at about 244±1° C.

In another embodiment, Form $H_B$ of Compound X has gradual loss of mass via TGA amounting to about 8.5% loss by 122° C.

The presence of reaction impurities and/or processing impurities may be determined by analytical techniques known in the art, such as, for example, chromatography, nuclear magnetic resonance spectroscopy, mass spectrometry, or infrared spectroscopy.

In one aspect of the invention, the polymorphs of the invention have crystalline properties and are preferably at least 50% crystalline, more preferably at least 60% crystalline, still more preferably at least 70% crystalline and most preferably at least 80% crystalline. Crystallinity can be estimated by conventional X-ray diffractometry techniques.

In some embodiments, the solid form of Compound X comprises one or more of the Forms described herein. A solid form of Compound X can include two or more of these Forms, i.e., it can be a mixture of two or more Forms. In some embodiments, a sample of the solid form mainly consists of a single Form selected from Forms A, $H_A$, and $H_B$ meaning that 50% or more of the material is of one solid Form. Relative amounts of various Forms in a mixture can be determined from XRPD data. As described herein, some of the Forms can evolve or interconvert under suitable conditions, such as Forms A and $H_A$, which can occur as a mixture, and can interconvert depending on the relative humidity and temperature at which the material is maintained.

In one aspect of the invention, the polymorphs of the invention are from 50%, 60%, 70%, 80% or 90% to 95%, 96%, 97%, 98%, 99% or 100% crystalline.

In the present specification, X-ray powder diffraction peaks (expressed in degrees 2θ) are measured using copper X-rays with a wavelength of 1.5406 Å (alpha1) and 1.5444 Å (alpha2).

The crystalline forms of the present invention can exist in either unsolvated or solvated forms. The term 'solvate' is used herein to describe a molecular complex comprising the compound of the invention and an amount of one or more pharmaceutically acceptable solvents. Examples of pharmaceutically acceptable solvents include ethanol and water. The term 'hydrate' is employed when the solvent is water. Two polymorphs of Compound X as described herein are hydrates.

In another embodiment, the crystalline form is Form A of Compound X, wherein said Form A contains less than 0.5% by weight of residual organic solvent.

In another embodiment, the crystalline form is Form A of Compound X, wherein said Form A contains less than 0.4% by weight of residual organic solvent.

In another embodiment, the crystalline form is Form A of Compound X, wherein said Form A contains less than 0.3% by weight of residual organic solvent.

In another embodiment, the crystalline form is Form A of Compound X, wherein said Form A contains less than 0.2% by weight of residual organic solvent.

In another embodiment, the crystalline form is Form A of Compound X, wherein said Form A contains less than 0.1% by weight of residual organic solvent.

In another embodiment, the crystalline form is Form $H_A$ of Compound X.

In another embodiment, the crystalline form is Form $H_B$ of Compound X.

In another embodiment, the crystalline form is Form A of Compound X in combination with Form $H_A$ of Compound X.

In another embodiment, the crystalline form is Form A of Compound X in combination with Form $H_A$ of Compound X.

In another embodiment, the crystalline form is Form A of Compound X in combination with Form $H_B$ of Compound X.

In another embodiment, the crystalline form is Form A of Compound X in combination with Form $H_A$ of Compound X and Form $H_B$ of Compound X.

In another embodiment, the present invention provides a composition comprising one solid form selected from any of the embodiment described above.

In another embodiment, the present invention provides a pharmaceutical composition comprising one solid form selected from any of the embodiment described above and at least one pharmaceutically acceptable carrier, diluent or excipient.

In another embodiment, the present invention provides a pharmaceutical composition, comprising a therapeutically effective amount of one solid form selected from any of the embodiment described above and at least one pharmaceutically acceptable carrier, diluent or excipient.

The pharmaceutical composition is useful in the treatment of diseases or disorders mediated by EED and/or PRC2.

In another embodiment, the present invention provides a pharmaceutical composition as defined above further comprising additional therapeutic agent(s).

In another embodiment, the present invention provides one solid form selected from any of the embodiment described above, for use in therapy, alone, or optionally in combination with another compound of the present invention and/or at least one other type of therapeutic agent.

In another embodiment, the present invention provides one solid form selected from any of the embodiments described above, for use in therapy, for the treatment of diseases or disorders mediated by EED and/or PRC2, alone, and/or at least one other type of therapeutic agent.

In another embodiment, the present invention provides a method for the treatment of diseases or disorders mediated by EED and/or PRC2, comprising administering to a patient in need of such treatment a therapeutically effective amount of one solid form selected from any of the embodiments described above, alone, and/or at least one other type of therapeutic agent.

In another embodiment, the present invention provides a method for the treatment of diseases or disorders mediated by EED and/or PRC2, comprising administering to a patient in need thereof a therapeutically effective amount of a first and second therapeutic agent, wherein the first therapeutic agent is one solid form selected from any of the embodiments described above, and the second therapeutic agent is one other type of therapeutic agent.

In another embodiment, the present invention also provides the use of one solid form selected from any of the embodiments described above, for the manufacture of a medicament for the treatment of diseases or disorders mediated by EED and/or PRC2, alone, or optionally in combination with at least one other type of therapeutic agent.

In another embodiment, the present invention provides a combined preparation of one solid form selected from any of the embodiments described above and additional therapeutic agent(s) for use in therapy.

In another embodiment, the present invention provides a combination of one solid form selected from any of the embodiments described above and additional therapeutic agent(s) for simultaneous or separate use in therapy.

In another embodiment, the present invention provides a combined preparation of one solid form selected from any of the embodiments described above and additional therapeutic agent(s) for simultaneous, separate or sequential use in the treatment of diseases or disorders mediated by EED and/or PRC2. Said solid form may be administered as a pharmaceutical composition described herein.

Examples of diseases or disorders mediated by EED and/or PRC2 include, but are not limited to, diffused large B cell lymphoma (DLBCL), follicular lymphoma, other lymphomas, leukemia, multiple myeloma, mesothelioma, gastric cancer, malignant rhabdoid tumor, hepatocellular carcinoma, prostate cancer, breast carcinoma, bile duct and gallbladder cancers, bladder carcinoma, brain tumors including neurobalstoma, glioma, glioblastoma and astrocytoma, cervical cancer, colon cancer, melanoma, endometrial cancer, esophageal cancer, head and neck cancer, lung cancer, nasopharhyngeal carcinoma, ovarian cancer, pancreatic cancer, renal cell carcinoma, rectal cancer, thyroid cancers, parathyroid tumors, uterine tumors, and soft tissue sarcomas selected from rhabdomyosarcoma (RMS), Kaposi sarcoma, synovial sarcoma, osteosarcoma and Ewing's sarcoma.

In another embodiment, the present invention provides a method for the treatment of diseases or disorders mediated by EED and/or PRC2, comprising administering to a patient in need thereof a therapeutically effective amount of a first therapeutic agent optionally with a second therapeutic agent, wherein the first therapeutic agent is one solid form selected from any of the embodiments described above and the second therapeutic agent is one other type of therapeutic agent; wherein the diseases or disorders are selected from diffused large B cell lymphoma (DLBCL), follicular lymphoma, other lymphomas, leukemia, multiple myeloma, gastric cancer, malignant rhabdoid tumor, and hepatocellular carcinoma.

In another embodiment, additional therapeutic agent(s) used in combined pharmaceutical compositions or combined methods or combined uses, are selected from one or more, preferably one to three, of the following therapeutic agents: other anti-cancer agents, immunomodulators, anti-allergic agents, anti-nausea agents (or anti-emetics), pain relievers, cytoprotective agents, and combinations thereof.

In another embodiment, the present invention provides a process of preparing crystalline Form A of Compound X, wherein said Form A contains less than 0.5% by weight of residual organic solvent, preferably less than 0.2% by weight of residual organic solvent, more preferably less than 0.1% by weight of residual organic solvent.

In another embodiment, the present invention provides a process of preparing crystalline Form A of Compound X, comprising the steps:
1) suspending N-((5-Fluoro-2,3-dihydrobenzofuran-4-yl)methyl)-8-(2-methylpyridin-3-yl)-[1,2,4]triazolo[4,3-c]pyrimidin-5-amine (Compound A) in a mixture of water and water-miscible organic solvent;
2) heating the resulting suspension to at least about 50° C.;
3) acidifying the resulting suspension to form a clear solution while maintaining the temperature at least about 50° C.; and
4) lowering the temperature of the resulting solution to prompt formation of crystals to obtain Form A of Compound X.

In another embodiment, the present invention a process of preparing crystalline Form A of Compound X that contains less than 0.5% by weight of residual organic solvent, preferably less than 0.3% weight of residual organic solvent, more preferably less than 0.1% weight of residual organic solvent, comprising the steps:
1) suspending N-((5-Fluoro-2,3-dihydrobenzofuran-4-yl)methyl)-8-(2-methylpyridin-3-yl)-[1,2,4]triazolo[4,3-c]pyrimidin-5-amine (Compound A) in a mixture of water and water-miscible organic solvent;
2) heating the resulting suspension to about or over 50° C.;
3) acidifying the resulting suspension to form a clear solution while maintaining the temperature at at about or over 50° C.; and
4) lowering the temperature of the resulting solution to prompt formation of crystals to obtain Form A of Compound X.

In another embodiment, the present invention provides a process of preparing crystalline Form A of Compound X that contains less than 0.5% by weight of residual organic solvent, comprising the steps:
1) suspending Compound A in a mixture of water and water-miscible organic solvent selected from a group consisting of ethanol and acetone;
2) heating the resulting suspension to about 50 to 75° C.;
3) acidifying the resulting suspension to form a clear solution by adding a solution of 0.5 N HCl in a mixture of water and said water-miscible organic solvent, while maintaining the temperature about 50 to 75° C.; and
4) lowering the temperature of the solution to prompt formation of crystals to obtain Form A of Compound X.

In another embodiment, the present invention provides crystalline Form A of Compound X obtained by a process comprising the steps:
1) suspending N-((5-Fluoro-2,3-dihydrobenzofuran-4-yl)methyl)-8-(2-methylpyridin-3-yl)-[1,2,4]triazolo[4,3-c]pyrimidin-5-amine (Compound A) in a mixture of water and water-miscible organic solvent;
2) heating the resulting suspension to about or over 50° C.;
3) acidifying the resulting suspension to form a clear solution while maintaining the temperature at about or over 50° C.; and
4) lowering the temperature of the resulting solution to prompt formation of crystals to obtain Form A of Compound X.

In another embodiment, the present invention provides crystalline Form A of Compound X that contains less than 0.5% by weight of residual organic solvent, preferably less than 0.3% weight of residual organic solvent, more preferably less than 0.1% weight of residual organic solvent, obtained by a process comprising the steps:
1) suspending N-((5-Fluoro-2,3-dihydrobenzofuran-4-yl)methyl)-8-(2-methylpyridin-3-yl)-[1,2,4]triazolo[4,3-c]pyrimidin-5-amine (Compound A) in a mixture of water and water-miscible organic solvent;
2) heating the resulting suspension to about or over 50° C.;
3) acidifying the resulting suspension to form a clear solution while maintaining the temperature at about or over 50° C.; and
4) lowering the temperature of the resulting solution to prompt formation of crystals to obtain Form A of Compound X.

In another embodiment, the present invention provides crystalline Form A of Compound X that contains less than 0.5% by weight of residual organic solvent, preferably less than 0.3% weight of residual organic solvent, more preferably less than 0.1% weight of residual organic solvent, obtained by a process comprising the steps:
1) suspending Compound A in a mixture of water and water-miscible organic solvent selected from a group consisting of ethanol and acetone;
2) heating the resulting suspension to about 50 to 75° C.;
3) acidifying the resulting suspension to form a clear solution by adding a solution of 0.5 N HCl in a mixture of water and said water-miscible organic solvent, while maintaining the temperature at about 50 to 75° C.; and
4) lowering the temperature of the solution to prompt formation of crystals to obtain Form A of Compound X.

In another embodiment, the present invention provides crystalline Form A of Compound X obtainable by a process comprising the steps:
1) suspending N-((5-Fluoro-2,3-dihydrobenzofuran-4-yl)methyl)-8-(2-methylpyridin-3-yl)-[1,2,4]triazolo[4,3-c]pyrimidin-5-amine (Compound A) in a mixture of water and water-miscible organic solvent;
2) heating the resulting suspension to about or over 50° C.;
3) acidifying the resulting suspension to form a clear solution while maintaining the temperature at about or over 50° C.; and 4) lowering the temperature of the resulting solution to prompt formation of crystals to obtain Form A of Compound X.

In another embodiment, the present invention provides crystalline Form A of Compound X that contains less than 0.5% by weight of residual organic solvent, preferably less than 0.3% weight of residual organic solvent, more preferably less than 0.1% weight of residual organic solvent, obtained by a process comprising the steps:
1) suspending N-((5-Fluoro-2,3-dihydrobenzofuran-4-yl)methyl)-8-(2-methylpyridin-3-yl)-[1,2,4]triazolo[4,3-c]pyrimidin-5-amine (Compound A) in a mixture of water and water-miscible organic solvent;
2) heating the resulting suspension to about or over 50° C.;
3) acidifying the resulting suspension to form a clear solution while maintaining the temperature at about or over 50° C.; and
4) lowering the temperature of the resulting solution to prompt formation of crystals to obtain Form A of Compound X.

In another embodiment, the present invention provides crystalline Form A of Compound X that contains less than 0.5% by weight of residual organic solvent, preferably less than 0.3% weight of residual organic solvent, more preferably less than 0.1% weight of residual organic solvent, obtainable by a process comprising the steps steps:
1) suspending Compound A in a mixture of water and water-miscible organic solvent selected from a group consisting of ethanol and acetone;
2) heating the resulting suspension to about 50 to 75° C.;
3) acidifying the resulting suspension to form a clear solution by adding a solution of 0.5 N HCl in a mixture of water and said water-miscible organic solvent, while maintaining the temperature about 50 to 75° C.; and
4) lowering the temperature of the solution to prompt formation of crystals to obtain Form A of Compound X.

In another embodiment, the present invention provides a process of preparing crystalline Form A of Compound X, comprising the steps:
1) suspending N-((5-Fluoro-2,3-dihydrobenzofuran-4-yl)methyl)-8-(2-methylpyridin-3-yl)-[1,2,4]triazolo[4,3-c]pyrimidin-5-amine (Compound A) in a mixture of water and water-miscible organic solvent;
2) heating the resulting suspension to at least about 50° C.;
3) acidifying the resulting suspension to form a clear solution with hydrochloric acid while maintaining the temperature at least about 50° C.; and
4) lowering the temperature of the resulting solution to prompt formation of crystals to obtain Form A of Compound X.

In another embodiment, the present invention a process of preparing crystalline Form A of Compound X that contains less than 0.5% by weight of residual organic solvent, preferably less than 0.3% weight of residual organic solvent, more preferably less than 0.1% weight of residual organic solvent, comprising the steps:
1) suspending N-((5-Fluoro-2,3-dihydrobenzofuran-4-yl)methyl)-8-(2-methylpyridin-3-yl)-[1,2,4]triazolo[4,3-c]pyrimidin-5-amine (Compound A) in a mixture of water and water-miscible organic solvent;
2) heating the resulting suspension to about or over 50° C.;
3) acidifying the resulting suspension with hydrochloric acid to form a clear solution while maintaining the temperature at at about or over 50° C.; and
4) lowering the temperature of the resulting solution to prompt formation of crystals to obtain Form A of Compound X.

In another embodiment, the present invention provides a process of preparing crystalline Form A of Compound X that contains less than 0.5% by weight of residual organic solvent, comprising the steps:
1) suspending Compound A in a mixture of water and water-miscible organic solvent selected from a group consisting of ethanol and acetone;
2) heating the resulting suspension to about 50 to 75° C.;
3) acidifying the resulting suspension with hydrochloric acid to form a clear solution by adding a solution of 0.5 N HCl in a mixture of water and said water-miscible organic solvent, while maintaining the temperature about 50 to 75° C.; and
4) lowering the temperature of the solution to prompt formation of crystals to obtain Form A of Compound X.

In another embodiment, the present invention provides crystalline Form A of Compound X obtained by a process comprising the steps:
1) suspending N-((5-Fluoro-2,3-dihydrobenzofuran-4-yl)methyl)-8-(2-methylpyridin-3-yl)-[1,2,4]triazolo[4,3-c]pyrimidin-5-amine (Compound A) in a mixture of water and water-miscible organic solvent;
2) heating the resulting suspension to about or over 50° C.;
3) acidifying the resulting suspension with hydrochloric acid to form a clear solution while maintaining the temperature at about or over 50° C.; and
4) lowering the temperature of the resulting solution to prompt formation of crystals to obtain Form A of Compound X.

In another embodiment, the present invention provides crystalline Form A of Compound X that contains less than 0.5% by weight of residual organic solvent, preferably less than 0.3% weight of residual organic solvent, more preferably less than 0.1% weight of residual organic solvent, obtained by a process comprising the steps:
1) suspending N-((5-Fluoro-2,3-dihydrobenzofuran-4-yl)methyl)-8-(2-methylpyridin-3-yl)-[1,2,4]triazolo[4,3-c]pyrimidin-5-amine (Compound A) in a mixture of water and water-miscible organic solvent;
2) heating the resulting suspension to about or over 50° C.;
3) acidifying the resulting suspension with hydrochloric acid to form a clear solution while maintaining the temperature at about or over 50° C.; and 4) lowering the temperature of the resulting solution to prompt formation of crystals to obtain Form A of Compound X.

In another embodiment, the present invention provides crystalline Form A of Compound X that contains less than 0.5% by weight of residual organic solvent, preferably less than 0.3% weight of residual organic solvent, more preferably less than 0.1% weight of residual organic solvent, obtained by a process comprising the steps:
1) suspending Compound A in a mixture of water and water-miscible organic solvent selected from a group consisting of ethanol and acetone;
2) heating the resulting suspension to about 50 to 75° C.;
3) acidifying the resulting suspension with hydrochloric acid to form a clear solution by adding a solution of 0.5 N HCl in a mixture of water and said water-miscible organic solvent, while maintaining the temperature at about 50 to 75° C.; and
4) lowering the temperature of the solution to prompt formation of crystals to obtain Form A of Compound X.

In another embodiment, the present invention provides crystalline Form A of Compound X obtainable by a process comprising the steps:
1) suspending N-((5-Fluoro-2,3-dihydrobenzofuran-4-yl)methyl)-8-(2-methylpyridin-3-yl)-[1,2,4]triazolo[4,3-c]pyrimidin-5-amine (Compound A) in a mixture of water and water-miscible organic solvent;
2) heating the resulting suspension to about or over 50° C.;
3) acidifying the resulting suspension with hydrochloric acid to form a clear solution while maintaining the temperature at about or over 50° C.; and
4) lowering the temperature of the resulting solution to prompt formation of crystals to obtain Form A of Compound X.

In another embodiment, the present invention provides crystalline Form A of Compound X that contains less than 0.5% by weight of residual organic solvent, preferably less than 0.3% weight of residual organic solvent, more preferably less than 0.1% weight of residual organic solvent, obtained by a process comprising the steps:
1) suspending N-((5-Fluoro-2,3-dihydrobenzofuran-4-yl)methyl)-8-(2-methylpyridin-3-yl)-[1,2,4]triazolo[4,3-c]pyrimidin-5-amine (Compound A) in a mixture of water and water-miscible organic solvent;
2) heating the resulting suspension to about or over 50° C.;
3) acidifying the resulting suspension to form a clear solution while maintaining the temperature at about or over 50° C.; and
4) lowering the temperature of the resulting solution to prompt formation of crystals to obtain Form A of Compound X.

In another embodiment, the present invention provides crystalline Form A of Compound X that contains less than 0.5% by weight of residual organic solvent, preferably less than 0.3% weight of residual organic solvent, more preferably less than 0.1% weight of residual organic solvent, obtainable by a process comprising the steps steps:
1) suspending Compound A in a mixture of water and water-miscible organic solvent selected from a group consisting of ethanol and acetone;
2) heating the resulting suspension to about 50 to 75° C.;
3) acidifying the resulting suspension with hydrochloric acid to form a clear solution by adding a solution of 0.5 N HCl in a mixture of water and said water-miscible organic solvent, while maintaining the temperature about 50 to 75° C.; and
4) lowering the temperature of the solution to prompt formation of crystals to obtain Form A of Compound X.

In further embodiments to the above processes of preparing crystalline Form A of Compound X, the present invention provides the following preferred ratios of the solvent mixture:
A ratio of solvent mixture of $H_2O$ and EtOH wherein EtOH is 80 to 100% by weight.
A ratio of solvent mixture of $H_2O$ and EtOH wherein EtOH is 85 to 100% by weight.
A ratio of solvent mixture of $H_2O$ and EtOH wherein EtOH is 90 to 100% by weight.
A ratio of solvent mixture of $H_2O$ and EtOH wherein EtOH is 95 to 100% by weight.
A ratio of solvent mixture of $H_2O$ and EtOH wherein EtOH is 85 to 95% by weight.
A ratio of solvent mixture of $H_2O$ and EtOH wherein EtOH is 90 to 95% by weight.

In further embodiments to the above processes of preparing crystalline Form A of Compound X, the present invention provides the following preferred temperature ranges for step 2:
A temperature range is 50 to 75° C.
A temperature range is 60 to 75° C.
A temperature range is 70 to 75° C.

Various (enumerated) embodiments of the invention are described herein. It will be recognized that features specified in each embodiment may be combined with other specified features to provide further embodiments of the present invention. It is also understood that each individual element of the embodiments is its own independent embodiment.

Other features of the present invention should become apparent in the course of the above descriptions of exemplary embodiments that are given for illustration of the invention and are not intended to be limiting thereof.

III. DEFINITIONS

The general terms used hereinbefore and hereinafter preferably have within the context of this invention the following meanings, unless otherwise indicated, where more general terms wherever used may, independently of each other, be replaced by more specific definitions or remain, thus defining more detailed embodiments of the invention.

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

The term "a," "an," "the" and similar terms used in the context of the present invention (especially in the context of the claims) are to be construed to cover both the singular and plural unless otherwise indicated herein or clearly contradicted by the context.

All numbers expressing quantities of ingredients, weight percentages, temperatures, and so forth that are preceded by the word "about" are to be understood as only approximations so that slight variations above and below the stated number may be used to achieve substantially the same results as the stated number. Accordingly, unless indicated to the contrary, numerical parameters preceded by the word "about" are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The names used herein to characterize a specific form, e.g., "$H_4$" etc., are merely identifiers that are to be interpreted in accordance with the characterization information presented herein and are not to be limited so as to exclude any other substance possessing similar or identical physical and chemical characteristics.

All measurements are subject to experimental error and are within the spirit of the invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The phrase "pharmaceutically acceptable" indicates that the substance or composition must be compatible chemically and/or toxicologically, with the other ingredients comprising a formulation, and/or the mammal being treated therewith.

Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., Remington: The Science and Practice of Pharmacy, 22nd Edition, Pharmaceutical Press, London, UK (2012), the invention of which is hereby incorporated by reference.

As used herein, "polymorph(s)" refer to crystalline form(s) having the same chemical structure/composition but different spatial arrangements of the molecules and/or ions forming the crystals.

As used herein "amorphous" refers to a solid form of a molecule, atom, and/or ions that is not crystalline. An amorphous solid does not display a definitive X-ray diffraction pattern.

For pharmacopeial purposes, "residual organic solvents" in pharmaceuticals are defined as organic volatile chemicals that are used or produced in the manufacture of drug substances or excipients, or in the preparation of drug products. The residual organic solvents are not completely removed by practical manufacturing techniques.

As used herein, "water-miscible organic solvent" refers to an organic solvent that is liquid at room temperature and is completely miscible with water, preferably is selected from ethanol and acetone.

As used herein, a XRPD pattern "comprising" a number of peaks selected from a specified group of peaks, is intended to include XRPD patterns having additional peaks that are not included in the specified group of peaks.

"EED" refers to the protein product of the gene embryonic ectoderm development.

"PRC2" refers to Polycomb Repressive Complex 2.

The term "PRC2-mediated disease or disorder" refers to any disease or disorder which is directly or indirectly regulated by PRC2. This includes, but is not limited to, any disease or disorder which is directly or indirectly regulated by EED.

The term "diseases or disorders mediated by EED and/or PRC2" refers to diseases or disorders which are directly or indirectly regulated by EED and/or PRC2.

As used herein, the term "patient" encompasses all mammalian species.

As used herein, the term "subject" refers to an animal. Typically the animal is a mammal. A "subject" also refers to any human or non-human organism that could potentially benefit from treatment with an EED inhibitor. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human. Exemplary subjects include human beings of any age with risk factors for cancer disease.

As used herein, a subject is "in need of" a treatment if such subject would benefit biologically, medically or in quality of life from such treatment (preferably, a human).

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat', "treating" or "treatment" of any disease/disorder refers to the treatment of the disease/disorder in a mammal, particularly in a human, and includes: (a) ameliorating the disease/disorder, (i.e., slowing or arresting or reducing the development of the disease/disorder, or at least one of the clinical symptoms thereof); (b) relieving or modulating the disease/disorder, (i.e., causing regression of the disease/disorder, either physically, (e.g., stabilization of a discernible symptom), physiologically, (e.g., stabilization of a physical parameter), or both); (c) alleviating or ameliorating at least one physical parameter including those which may not be discernible by the subject; and/or (d) preventing or delaying the onset or development or progression of the disease or disorder from occurring in a mammal, in particular, when such mammal is predisposed to the disease or disorder but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" or "reducing risk" covers therapies that lower the incidence of development of a clinical disease state. As such, primary and secondary prevention therapies are examples of risk reduction.

"Therapeutically effective amount" is intended to include an amount of a compound of the present invention that will elicit the biological or medical response of a subject, for example, reduction or inhibition of EED and/or PRC2, or ameliorate symptoms, alleviate conditions, slow or delay disease progression, or prevent a disease or disorder mediated by PRC2. When applied to a combination, the term refers to combined amounts of the active ingredients that result in the preventive or therapeutic effect, whether administered in combination, serially, or simultaneously.

Abbreviations as used herein, are defined as follows: "EtOH" for ethanol, "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for aqueous, "sat" or "sat'd" for saturated, "MW" for molecular weight, "mw" or "μwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LC-MS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, "ee" for "enantiomeric excess" and "α", "β", "R", "S", "E", and "Z" are stereochemical designations familiar to one skilled in the art.

General Methods

The following methods were used in the exemplified Examples, except where noted otherwise.

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be compiled or passed through a mesh screen to delump the product, if necessary.

Crystalline forms may be prepared directly from the reaction medium of the final process for preparing Compound X. This may be achieved, for example, by employing in the final process step a solvent or a mixture of solvents from which Compound (I) may be crystallized. Alternatively, crystalline forms may be obtained by distillation or solvent addition techniques. Suitable solvents for this purpose include, for example, the aforementioned nonpolar solvents and polar solvents, including protic polar solvents such as alcohols, and aprotic polar solvents such as ketones.

X-Ray Powder Diffraction (XRPD)

X-ray powder diffraction (XRPD) data were obtained using a Bruker D8 Discover with CuKα anode. Powder samples were placed on a glass slide and centered in the X-ray beam. The sample-detector distance was around 30 cm, three frames merged. The radiation was CuKα (λ=1.5418 Å). Data were collected for 2<2θ<45° with a sample exposure time of at least 270 seconds.

The derived atomic parameters (coordinates and temperature factors) were refined through full matrix least-squares. The function minimized in the refinements was $\Sigma_w(|F_o|-|F_c|)^2$. R is defined as $\Sigma||F|-|F||/\Sigma|F_o|$ while $R_w=[\Sigma_w(|F_o|-|F_c|)^2/\Sigma_w |F_o|^2]^{1/2}$ where w is an appropriate weighting function based on errors in the observed intensities. Difference maps were examined at all stages of refinement. Hydrogen atoms were introduced in idealized positions with isotropic temperature factors, but no hydrogen parameters were varied.

| | |
|---|---|
| Instrument | Bruker AXS DiscoverD8 |
| Detector | PXC-VANTEC-500 |
| Radiation | CuKα (0.15406 nm) |
| X-ray generator power | 40 kV, 40 mA |
| Scan range | 2° to 45° (2 theta value) |
| Scan time | 90 s/frame, 3 frames |
| X-ray optics | Monochromator |
| Detector distance | ~30 cm |

Thermogravimetric Analysis

Thermogravimetric analysis was conducted for each crystalline form using a TA Discovery TGA instrument. For each analysis, the TGA cell/sample chamber was purged with 20 ml/min of ultra-high purity nitrogen gas. A weight calibration was performed using standard weights under nitrogen purge. The heating rate was 10° C. per minute in the temperature range between rt and 300° C. The weight percentage change (wt %) was plotted versus the measured sample temperature.

Differential Scanning Calorimetry

Differential scanning calorimetry was conducted for each crystalline form using a TA Discovery DSC. For each analysis, the DSC cell/sample chamber was purged with 50 ml/min of ultra-high purity nitrogen gas. The instrument was calibrated with high purity indium. The heating rate was 10° C. per minute in the temperature range between 30 and 300° C. The heat flow, which was normalized by sample weight, was plotted versus the measured sample temperature. The data were reported in units of watts/gram ("W/g"). The plot was made with the endothermic peaks pointing down. The endothermic melt peak (melting point) was evaluated for extrapolated onset temperature.

Dynamic Vapor Sorption

Dynamic vapor sorption was performed on a Surface Measurement Systems DVS Advantage instrument. Approximately 10 mg of material was loaded into a sample pan. The samples were exposed to sorption/desorption cycles in 10% relative humidity (RH) steps over the range of 50%-90%-0%-90%-50% RH at 25° C. and 50° C. A target equilibrium condition of mass change less than 0.002% over 5 min was set, with minimum and maximum equilibrium periods of 10 and 360 min, respectively. The carrier gas was nitrogen with a flow rate of 100 mL/min. The system is calibrated with saturated salt solutions. The weight percentage change (wt %) of the sample at each stage was measured and plotted versus the target partial pressure.

| TGA | |
|---|---|
| Instrument | TA Discovery TGA |
| Temperature range | 30-300° C. |
| Scan rate | 10 K/min |
| Nitrogen flow | 25 mL/min |

| DSC | |
|---|---|
| Instrument | TA Discovery DSC |
| Temperature range | 30° C.-300° C. |
| Scan rate | 10 K/min |
| Nitrogen flow | 50 mL/min |

| DVS | |
|---|---|
| Instrument | SMS DVS Advantage |
| Sample weight | About 10 mg |
| temperature | 25° C. and 50° C. |
| dm/dt | 0.002%/min |

NMR Employed in Characterization of Examples $^1$H NMR spectra were obtained with Bruker Fourier transform spectrometers operating at frequencies as follows: $^1$H NMR: 400 MHz (Bruker). $^{13}$C NMR: 100 MHz (Bruker). Spectra data are reported in the format: chemical shift (multiplicity, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for CD$_2$HSOCD$_3$, 3.30 ppm for CD$_2$HOD, 1.94 for CD$_3$CN, and 7.24 ppm for CDCl$_3$, and which in $^{13}$C NMR spectra appear at 39.7 ppm for CD$_3$SOCD$_3$, 49.0 ppm for CD$_3$OD, and 77.0 ppm for CDCl$_3$. All $^{13}$C NMR spectra were proton decoupled. The measurements were carried out at room temperature or otherwise specified. The amount of solvent residue was calculated based on intergrations of most representative hydrogens in the corresponding $^1$HNMR spectra.

V. EXAMPLES

The following Examples have been prepared, isolated and characterized using the methods disclosed herein. The following examples are not meant to be limiting of the scope of the invention.

Example 1: Preparation of Compound A (N-((5-Fluoro-2,3-dihydrobenzofuran-4-yl)methyl)-8-(2-methylpyridin-3-yl)-[1,2,4]triazolo[4,3-c]pyrimidin-5-amine) Intermediate 3: 8-bromo-5-(methylthio)-[1,2,4]triazolo[4,3-c]pyrimidine

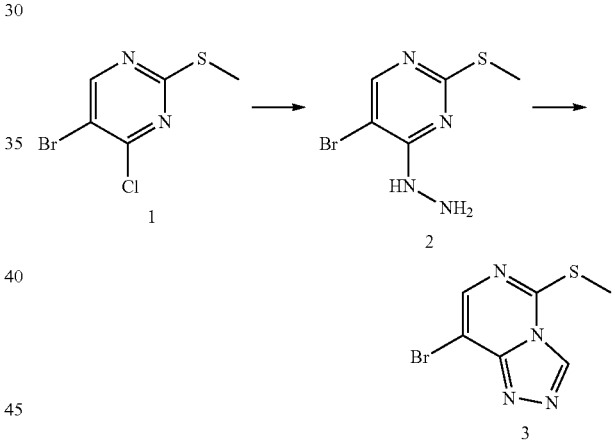

5-Bromo-4-hydrazinyl-2-(methylthio)pyrimidine (2): To a solution of 5-bromo-4-chloro-2-(methylthio)pyrimidine (1, 49.0 g, 0.205 mol) in ethanol (1000 mL) was added hydrazine (21.5 g, 0.430 mol). The reaction was stirred at rt for 4 h. The resulting suspension was filtered, washed with hexane and dried in vacuum to give the title compound (44.1 g, 92%) as a white solid. $^1$H-NMR (400 MHz, DMSO-d$_6$) δ ppm 2.42 (s, 3H), 8.08 (s, 1H). LC-MS: [M+H]$^+$=234.9; 236.9.

Intermediate 3: 5-bromo-4-hydrazinyl-2-(methylthio)pyrimidine (2) (40.0 g, 0.17 mol) was dissolved in 200 mL triethoxymethane. The mixture was heated at reflux and stirred for 3 h. The reaction mixture was concentrated under reduced pressure, the residue was purified by flash chromatography (EA:PE=1:15-1:1) to give the title compound (38.3 g, 92%) as a white solid. $^1$H-NMR (400 MHz, methanol-d$_4$) δ ppm 2.82 (s, 3H), 8.03 (s, 1H), 8.87 (s, 1H). LC-MS: [M+H]$^+$=245.0; 247.0.

Intermediate A1: 8-bromo-N-((5-fluoro-2,3-dihydrobenzofuran-4-yl)methyl)-[1,2,4]triazolo[4,3-c]pyrimidin-5-amine

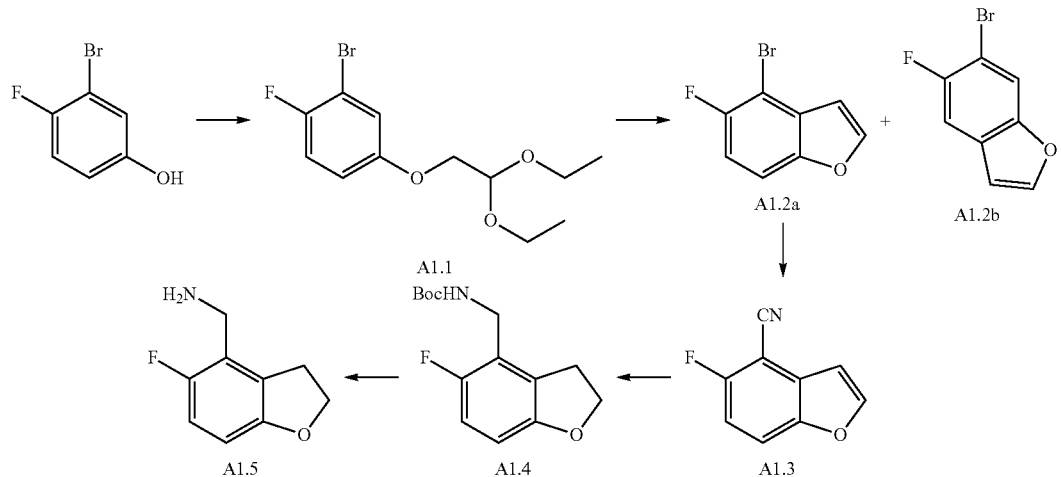

2-Bromo-4-(2,2-diethoxyethoxy)-1-fluorobenzene (A1.1): To a solution of 3-bromo-4-fluorophenol (500 g, 2.62 mol) and 2-bromo-1,1-diethoxyethane (670 g, 3.4 mol) in 2.0 L DMF was added $K_2CO_3$ (1085 g, 7.86 mol) in one portion. The suspension was heated at 110° C. and stirred overnight under $N_2$. After cooling to rt, the reaction was diluted with 10.0 L $H_2O$, and extracted with EtOAc (2.0 L×3). The combined organic phase was washed with brine twice, dried over anhydrous $Na_2SO_4$, filtered and concentrated under reduced pressure. The residue was purified on silica gel (EtOAc/hexane=0:100 to 5:100) to give the title compound (810 g, 80%) as a yellow oil. $^1$H-NMR (400 MHz, methanol-d4) δ ppm 1.27 (t, 6H), 3.65 (q, 2H), 3.78 (q, 2H), 3.97 (d, 2H), 4.82 (t, 1H), 3.97 (d, 2H), 6.84 (dd, 1H), 7.04 (dd, 1H), 7.13 (d, 1H).

4-Bromo-5-fluorobenzofuran (A1.2a along with regioisomer A1.2b): To a solution of PPA (1324 g, 3.93 mol) in toluene (2.0 L) was added A1.1 (810 g, 2.62 mol) over 30 min at 95° C. The reaction mixture was stirred at 95° C. for 2 h. After cooling to rt, 4.0 L ice-water was added slowly. The mixture was extracted with PE (2.0 L×2), the combined organic phase was washed with brine (2.0 L×2), dried over anhydrous $Na_2SO_4$, filtered and concentrated under reduced pressure. The residue was purified on silica gel (EtOAc/PE=0:100 to 5:100) to give a mixture of A1.2a and A1.2b (A1.2a A1.2b=1:0.7, 310 g, 55% yield) as a yellow oil.

5-Fluorobenzofuran-4-carbonitrile (A1.3): To a mixture of A1.2a and A1.2b (310 g, 1.44 mol) and $Zn(CN)_2$ (253 g, 2.16 mol) in 1.0 L DMF was added $Pd(PPh_3)_4$ (162 g, 0.14 mol) under $N_2$. The reaction mixture was heated at 100° C. and stirred for 18 h. After cooling to rt, the mixture was diluted with 5.0 L of water, and extracted with EtOAc (1.0 L×2). The combined organic phase was washed with brine (1 L), dried over $Na_2SO_4$ (anhydrous), filtered and concentration under reduced pressure. The residue was purified by flash column (mobile phase: EtOAc/PE=1:70 in 30 min, Ret. Time=11 min, flow rate: 120 mL/min) to give the title compound (92 g, 40%) as a white solid. $^1$H-NMR (400 MHz, methanol-d$_4$) δ ppm 7.07 (d, 1H), 7.30 (dd, 1H), 7.89 (dd, 1H), 8.10 (dd, 1H).

tert-Butyl ((5-fluoro-2,3-dihydrobenzofuran-4-yl)methyl)carbamate (A1.4): To a solution of A1.3 (44.5 g, 276.4 mmol) and $Boc_2O$ (90.0 g, 414.6 mmol) in 1.0 L MeOH was added Pd/C (5 g, 10% wt). The reaction mixture was degassed with $H_2$ and stirred under $H_2$ overnight. The mixture was filtered through celite, washed with MeOH (300 mL×2), the filtrate was concentrated under reduced pressure. The residue was recrystallized from PE to give the title compound (61.0 g, 93%) as a white solid. $^1$H-NMR (400 MHz, DMSO-d$_6$) δ ppm 1.38 (s, 9H), 3.21 (t, 2H), 4.12 (d, 2H), 4.53 (t, 2H), 6.63 (dd, 1H), 6.86 (dd, 1H), 7.25 (br s, 1H). LC-MS: [M-$^t$Bu+H]$^+$=212.1.

(5-Fluoro-2,3-dihydrobenzofuran-4-yl)methanamine (A1.5): A solution of A1.4 (18.3 g, 68.5 mmol) in 50 mL HCl/Dioxane (4 mol/L) was stirred at rt for 4 h. The mixture was concentrated under reduced pressure. The residue was diluted with a mixture solvent (MeOH:MeCN=1:10, 500 mL), then $K_2CO_3$ (18.0 g, 342.5 mmol) was added. The mixture was heated at 60° C. and stirred for 3 h, cooled to rt, filtered, and concentrated under reduced pressure. The crude product was purified on silica gel (MeOH:EtOAc=0:100 to 1:4) to give the title compound (9.2 g, 80%) as a yellow oil. $^1$H-NMR (400 MHz, methanol-d$_4$) δ ppm 3.27 (t, 2H), 3.77 (s, 2H), 4.56 (t, 2H), 6.59 (dd, 1H), 6.81 (dd, 1H). LC-MS: [M+H]$^+$=168.1.

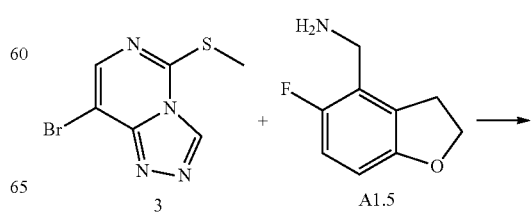

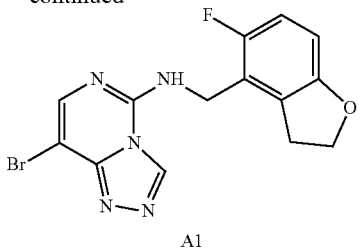

Intermediate A1: A mixture of A1.5 (1.41 g, 8.2 mmol) and 8-bromo-5-(methylthio)-[1,2,4]triazolo[4,3-c]pyrimidine (3) (1.0 g, 4.1 mmol) was heated at 40° C. and stirred for 16 h. After cooling to the rt, the mixture was diluted with EtOAc (35 mL). The precipitate was filtered and washed with EtOAc (3 mL×3), dried in vacuum to give the title compound (1.0 g, 67%) as a white solid. $^1$H NMR (500 MHz, DMSO) δ ppm 3.27 (t, 2H), 4.53 (t, 2H), 4.66 (d, 2H), 6.71 (dd, 1H), 6.95 (t, 1H), 7.85 (s, 1H), 8.75 (t, 1H), 9.48 (s, 1H). LC-MS: [M+H]$^+$=363.7; 365.7.

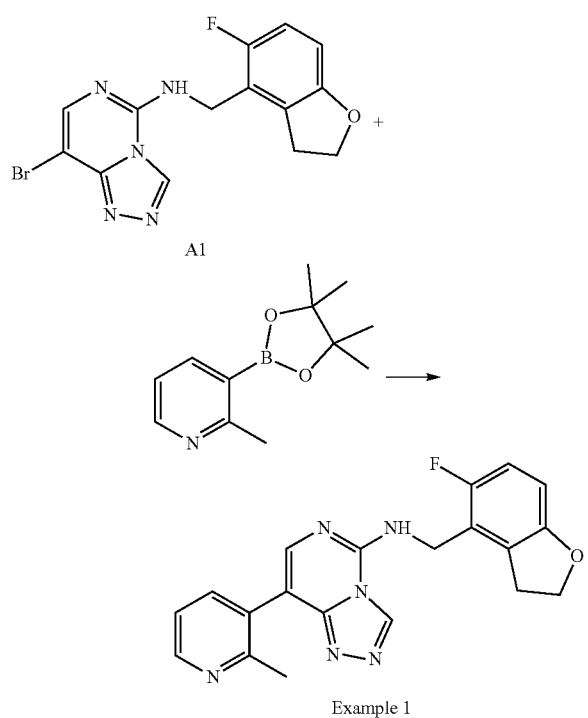

To a mixture of A1 (40 mg, 0.110 mmol) in 1,4-dioxane (3 mL), MeCN (0.30 mL) and water (0.30 mL) was added (2-methylpyridin-3-yl)boronic acid (30.1 mg, 0.220 mmol), potassium carbonate (45.5 mg, 0.330 mmol) and Pd(Ph$_3$P)$_4$ (12.69 mg, 10.98 μmol). The resulting mixture was stirred under N$_2$ at 110° C. for 3 h, cooled to rt, and evaporated under vacuum. The residue was purified on flash chromatography (DCM:MeOH=10:1) to afford N-((5-fluoro-2,3-dihydrobenzofuran-4-yl)methyl)-8-(2-methylpyridin-3-yl)-[1,2,4]triazolo[4,3-c]pyrimidin-5-amine as a white solid (20 mg, 46.0%).

Alternatively, N-((5-fluoro-2,3-dihydrobenzofuran-4-yl)methyl)-8-(2-methylpyridin-3-yl)-[1,2,4]triazolo[4,3-c]pyrimidin-5-amine was prepared as follows. To a suspension of A1 (25.5 g, 70 mmol), 2-methyl-3-(4,4,5,5-tetramethyl-1,3,2-dioxaborolan-2-yl)pyridine (30.6 g, 140 mmol) and NaHCO$_3$ (35.3 g, 420 mmol) in a mixture solution of 1,4-dioxane (300 mL) and H$_2$O (100 mL) was added PdCl$_2$(dppf) (5.94 g, 612 mmol). The mixture was degassed with N$_2$, heated at 110° C. for 1 h. The resulting mixture was cooled to rt and concentrated under reduced pressure. The residue was purified over column chromatography (EtOAc:MeOH=20:1) to give 14 g of the desired product. 200 mL of acetone was added to the product, and the resulting suspension was heated at 50° C. for 2 h. The white solid was collected by filtration and dried under vacuum to give N-((5-fluoro-2,3-dihydrobenzofuran-4-yl)methyl)-8-(2-methylpyridin-3-yl)-[1,2,4]triazolo[4,3-c]pyrimidin-5-amine (13.6 g, 52%)$^1$H-NMR (500 MHz, DMSO-d$_6$) δ ppm 2.40 (s, 3H), 3.33 (t, 2H), 4.56 (t, 2H), 4.72 (s, 2H), 6.72 (dd, 1H), 6.96 (dd, 1H), 7.31 (dd, 1H), 7.66 (s, 1H), 7.74 (d, 1H), 8.51 (d, 1H), 8.72 (t, 1H), 9.49 (s, 1H). LC-MS: [M+H]$^+$=376.9.

Example 2: Preparation of Form A of Compound X (N-((5-Fluoro-2,3-dihydrobenzofuran-4-yl)methyl)-8-(2-methylpyridin-3-yl)-[1,2,4]triazolo[4,3-c]pyrimidin-5-amine hydrochloride) using isopropanol (IPA) (Entry 1 in Table 2)

To a suspension of N-((5-fluoro-2,3-dihydrobenzofuran-4-yl)methyl)-8-(2-methylpyridin-3-yl)-[1,2,4]triazolo[4,3-c]pyrimidin-5-amine (6.0 g, 15.94 mmol) in 100 mL of IPA, a solution of 0.5 N HCl in IPA (33.0 mL, 16.50 mmol) was added dropwise at rt. The suspension was stirred at 50° C. for 12 h, then cooled to rt and stirred for 5 h. The resulting solid was collected by filtration, and dried at 40° C. under vacuum for 2 days to afford the hydrochloride salt of form A of compound X as a white solid (6.5 g, 98%) $^1$H NMR (DMSO-d$_6$) δ ppm 2.65 (s, 3H), 3.35 (t, 2H), 4.57 (t, 2H), 4.74 (d, 2H), 6.73 (dd, 1H), 6.97 (dd, 1H), 7.83 (s, 1H), 7.85-7.94 (m, 1H), 8.46 (d, 1H), 8.80 (dd, 1H), 9.07 (t, 1H), 9.58 (s, 1H). LC-MS: [M+H]$^+$=376.9. The amount of solvent residue was calculated based on intergrations of most representative hydrogens in the corresponding $^1$HNMR spectrum. Specifically, intergration at δ 1.04 accounting for 6 hydrogens of the methyl groups of IPA is 0.31, while that of 3 hydrogens of the methyl group at 2-methyl-pyridine at δ 2.64 as 3. Therefore, mole percentage of IPA is calculated as follows: 0.31/6 (1+0.31/6)=4.9%; while IPA percentage in weight is calculated as follows: 60×(0.31/6)/{(376.38+36.46+60×(0.31/6)}=0.74% {MW(IPA)=60, MW (compound A)=376.40 and MW (HCl)=36.46)}.

Example 3: Preparation of Form A of Compound X (N-((5-Fluoro-2,3-dihydrobenzofuran-4-yl)methyl)-8-(2-methylpyridin-3-yl)-[1,2,4]triazolo[4,3-c]pyrimidin-5-amine hydrochloride) using EtOH/H$_2$O (Entry 7 in Table 2)

To 4.0 g of N-((5-fluoro-2,3-dihydrobenzofuran-4-yl)methyl)-8-(2-methylpyridin-3-yl)-[1,2,4]triazolo[4,3-c]pyrimidin-5-amine in a 500 mL flask was added 200 mL of EtOH/H$_2$O (95/5, v/v), and the mixture was stirred by mechanical stirring. The resulting suspension was heated to 75° C. by oil bath and maintained at that temperature for 1 h. To the suspension maintained at 75° C., 23.38 mL of 0.5 N HCl in EtOH (1.1 eq) was added dropwisely. The mixture turned clear after the addition of hydrochloric acid. The resulting solution was stirred at 75° C. for 2 h. The mixture was then cooled down to rt in 3 h, and the resulting Compound X as a white solid (3.5 g, 79.7%) was collected by filtration and dried for 6 h under vacuum. The amount of EtOH residue was calculated based on the intergration of the hydrogen in the $^1$H NMR spectrum. Specifically, intergration at δ 1.06 accounting for 3 H of the methyl group of EtOH is 0.01, while that of 3 hydrogens of the methyl group at 2-methyl-pyridine at δ 2.65 as 3. Therefore, mole percentage of EtOH was calculated as follows: 0.01/3 (1+0.01/3)=0.33%; while EtOH percentage in weight is calculated as follows: 46.07×(0.01/3)/{(376.38+36.46+x (0.01/3)}=0.04% {MW(EtOH)=46.07, MW (compound A)=376.40 and MW (HCl)=36.46).

Example 4: Preparation of Form $H_A$ of Compound X 1.0 g of Form A of Compound X was added to 10 mL of ethanol/water (3:1) mixture to obtain a suspension. The suspension was stirred at rt for 3 days. The resulting solid was collected with vacuum filtration and dried at rt overnight. Form $H_A$ of Compound X (0.81 g) was obtained in 77% yield.

Example 5: Preparation of Form $H_B$ of Compound X 200 mg of Form A of Compound X was dissolved in minimum amount of acetone/water (1:1) mixtures at 60° C., to obtain a clear solution. The solution was evaporated at rt over 3 to 5 days. The resulting solid was collected with vacuum filtration and dried at rt overnight. Form $H_B$ of Compound X was obtained.
Preparation of 0.5 N HCl in EtOH or Acetone:
4.0 mL of the commercially available aqeuous concentrated HCl (36.5%, w/w, in water) was added to 96.0 mL of EtOH or acetone (optionally at reduced temperature), and the solution was mixed well to get 0.5 N HCl in EtOH or acetone.
Procedure for the Experiments Summarized in Table 2:
To 10 mg of compound X in a sample vial at 50° C., selected solvent was added dropwise. The addition of solvent was stopped when a clear solution was reached or when the amount of solvent reached 1 mL. The resulting mixture was stirred continuously at 50° C. for 2 h, then cooled to rt, and stirred overnight. The solubilities at 50° C. and rt were determined by the homogeneity of the resulting mixture.
Procedure for the Experiments Summarized in Table 3:
The experiments as Entries 1 to 6 in Table 3 were carried out according to the procedure described in the salt formation in Example 3 above, but with different parameters listed in the Table 3.

VI. PHARMACOLOGY AND UTILITY

As a key component of PRC2 complex, EED has no intrinsic enzymatic activity. However, it is critical for proper PRC2 function. EED directly binds to H3K27me3 and this binding event localizes the PRC2 complex to the chromatin substrate and allosterically activates the methyltransferase activity. Targeting the allosteric site within the regulatory EED subunit of PRC2, may offer a novel and unique angle to be advantageous to, or complementary to, directly targeting the SAM competition mechanism of EZH2 or PRC2. Therefore, targeting EED represents a highly attractive strategy for the development of a novel therapy for the treatment of many forms of cancers. In particular, the need exists for small molecules that inhibit the activity of PRC2 through targeting EED. It has now been found that triazolopyrimidine derivatives as presently disclosed are useful to target EED for the treatment of EED or PRC2-mediated diseases or disorders, especially cancers.

The utility of Compound X of the present invention may be demonstrated using any one of the following test procedures. Compound X was assessed for its ability to inhibit PRC2 activity in a pentameric complex of EZH2, SUZ12, EED, Rbap48 and AEBP in biochemical assays. The ability of compounds of the present invention to inhibit cellular activity of PRC2 was assessed by analysing histone H3 lysine 27 methylation in human cell lines. The ability of Compound X to inhibit cancers was derived from their ability to modulate activity in human cancer cell lines bearing specific dependence to PRC2 activity to maintain cancerous growth.
EED-H3K27Me3 Peptide Competition Binding Assay by AlphaScreen (α-Screen)

To assess the compounds' potency in the EED-H3K27Me3 competition binding assay, compounds were serially diluted 3-fold in DMSO to obtain a total of twelve concentrations. Then compounds at each concentration (75 nL of each) were transferred by Mosquito into a 384-well Perkin Elmer ProxiPlate 384 plus plates. 8 μL of solutions containing 30 nM EED (1-441)-His protein and 15 nM biotin-H3K27Me3 (19-33) peptide in the buffer (25 mM HEPES, pH 8, 0.02% Tween-20, 0.5% BSA) were added to the wells and then incubated with compound for 20 min. AlphaScreen detection beads mix was prepared immediately before use by mixing nickel chelate acceptor beads and streptavidin donor beads in a 1:1 ratio (Perkin Elmer, Product No. 6760619C/M/R) into the buffer described above. Then 4 μL of detection beads mix was added to the plate and incubate in the dark at the rt for 1 h. The final concentration of donor and acceptor beads was 10 μg/mL for each. Plates were read on EnVision (PerkinElmer) using the AlphaScreen setting adapted for optimal signal detection with a 615 nm filter, after sample excitation at 680 nm. The emission signal at 615 nm was used to quantify compounds inhibition. AlphaScreen signals were normalized based on the reading coming from the positive (maximum signal control) and negative controls (minimum signal control) to give percentage of activities left. The data were then fit to a dose response equation using the program Helios (Novartis) to get the IC50 values. Helios is a Novartis in-house assay data analysis software using the methods described by Normolle, D. P., Statistics in Medicine, 12:2025-2042 (1993); Formenko, I. et al, Computer Methods and Programs in Biomedicine, 82, 31-37 (2006); Sebaugh, J. L., Pharmaceutical Statistics, 10:128-134 (2011); Kelly, C. et al., Biometrics, 46(4):1071-1085 (1990); and Kahm, M. et al., Journal of Statistical Software, 33(7): (2010) (grofit: Fitting Biological Growth Curves with R, pages 1-21, available at http://www.jstatsoft.org/).

Each compound was counterscreened to determine if it interfered with the AlphaScreen beads. Compounds were diluted as described in the preceding section, and the assay was performed by adding 12 μL of 10 nM biotin-miniPEG-His6 peptide in the above buffer and incubating for 20 min at rt prior to addition of the beads to 10 μg/mL each. The plates were then incubated for 1 h at rt in dark before being read on EnVison.
EED LC-MS Assay Representative compounds of the present invention were serially and separately diluted 3-fold in DMSO to obtain a total of eight or twelve concentrations. Then the test compounds at each concentration (120 nL of each) were transferred by Mosquito into a 384-well Perkin Elmer ProxiPlate 384 plus plates. Solutions (6 µL) of 24 nM the wild type PRC2 (wtPRC2) complex and 2 µM SAM in reaction buffer (20 mM Tris, pH 8.0, 0.1% BSA, 0.01% Triton, 0.5 mM DTT) were added to the wells that were then incubated with the test compound for 20 min. A 6 µL solution of 3 µM of the peptide substrate H3K27Me0 (histone H3[21-44]-biotin) in reaction buffer was added to initiate each reaction. The final components in the reaction solution include 12 nM wtPRC2 complex, 1 µM SAM, and 1.5 µM H3K27me0 peptide with varying concentration of the compounds. A positive control consisted of the enzyme, 1 µM SAM and 1.5 µM substrate in the absence of the test compound, and a negative control consisted of 1 µM SAM and 1.5 µM substrate only. Each reaction was incubated at rt for 120 min, then stopped by addition of 3 µL per of quench solution (2.5% TFA with 320 nM d4-SAH). The reaction mixture was centrifuged (Eppendorf centrifuge 5810, Rotor A-4-62) for 2 min at 2000 rpm and read on an API 4000 triple quadrupole mass spec with Turbulon Spray (Applied Biosystem) coupled with Prominence UFLC (Shimadzu). The levels of SAH production were then normalized based on the values coming from the positive and negative controls to give percent enzyme activities. The data were then fit to a dose response equation using the program Helios to get the $IC_{50}$ values of the test compound.

ELISA (H3K27 Methylation) Assay

Representative compounds of the present invention were serially and separately diluted 3-fold in DMSO to obtain a total of eight or twelve concentrations. Then the compounds were added to G401 cell cultured in 384-well plate at 1:500 dilution to obtain the highest concentration of 20 µM. The cells were further cultured for 48 h before ELISA procedure.

Histone extraction: Cells, in 384-well plate, were washed with PBS (10×PBS buffer (80 g NaCl (Sigma, S3014), 2 g KCl (Sigma, 60128), 14.4 g $Na_2HPO_4$ (Sigma, S5136), 2.4 g $KH_2PO_4$ (Sigma, P9791) to 1 L water, pH to 7.4) and lysed with the addition of lysis buffer (0.4N HCl; 45 µL per well). The plate was gently agitated at 4° C. for 30 min. The cell lysate was neutralized with neutralization buffer (0.5 M sodium phosphate dibasic, pH 12.5, 1 mM DTT; 36 µL per well). The plate was agitated to ensure the lysates were well mixed prior to the ELISA protocol.

ELISA protocol: Cell lysates were transferred to the wells of a 384-well plate and the final volume was adjusted to 50 µL per well with PBS. The plate was sealed, centrifuged at 2,000 rpm for 2 min and incubated at 4° C. for about 16 h. The plate was washed with TBST buffer (1×TBS (10×TBS: 24.2 g Tris (Sigma, T6066), 80 g NaCl (Sigma, S3014) to 1 L of water and adjust pH to 7.6 with HCl) with 0.1% Tween-20). Blocking buffer (TBST, 5% BSA; 50 µL per well) was added and the plate was incubated for 1 h at rt. The blocking buffer was removed and primary antibody was added (30 µL per well). The following dilutions were performed with blocking buffer: for anti-H3K27me3 antibody (Cell Signaling Technology, #9733), dilution was 1:1000; for anti-H3K27me2 antibody (Cell Signaling Technology, #9288), dilution was 1:100; for anti-H3 antibody (Abcam, Cat #24834), dilution was 1:1000. The primary antibody was incubated in the plate at rt for 1 h. The wells were washed with TBST and incubated with secondary antibody for 1 h at rt. For secondary antibodies, the following dilutions were carried out with blocking buffer: anti-rabbit antibody (Jackson ImmunoResearch, #111-035-003), dilution was 1:2000; and anti-mouse antibody (Cell signaling technology, #7076), dilution was 1:1000. After 1 h of incubation at rt, the wells were washed with TBST. ECL substrate (Pierce, #34080) was added at 30 µL per well and the plates were centrifuged at 2,000 rpm for 2 min. The signal was read using a PerkinElmer Envision Reader. The H3K27 methylation readouts were normalized using H3 signal and then percentage inhibition was calculated against the samples treated with DMSO. The data were then fit to a dose response curve using the program Helios to get the $IC_{50}$ values of the test compound.

Western Blot Analysis

Representative compounds of the present invention were analyzed for their ability to selectively inhibit PRC2. Western blot was performed using standard molecular biology techniques. Cell was lysed in SDS lysis buffer (Millipore, Cat #20-163) and protein concentration was measured by BCA protein assay (Pierce, Cat #PI-23221). Antibodies for western blots: anti-EZH2 (#3147), anti-H3 (#9715), anti-H3K4me1 (#9723), anti-H3K4me2 (#9725), anti-H3K4me3 (#9727), anti-H3K9me2 (#9753), anti-H3K36me2 (#9758), anti-H3K27me2 (#9755), and anti-H3K27me3 (#9756) were purchased from Cell Signaling Technology (Danvers, Mass., USA). Anti-H3K9me1 (#07-395), anti-H3K27me1 (#07-448), and anti-H3K36me1 (#07-548) were purchased from Millipore (Billerica, Mass., USA). Anti-H3K36me3 (ab9050-100) was purchased from Abcam (Cambridge, UK). Anti-H3K9me3 (#39161) was purchased from Active Motif (Carlsbad, Calif., USA).

Compounds of the present invention specifically inhibit the methylation of the PRC2 substrate H3K27. This can be demonstrated by their ability to inhibit H3K27me2 and H3K27me3 in a number of human cancer cell lines, examples include rhabdoid cells (G401) and lymphoma cells (WSU-DLCL2, KARPAS422, SU-DHL4). Selectivity is profiled against a number of other methylation marks, for example: H3K4me2; H3K9me2; H3K36me3; and H3K79me3.

Analysis of Cell Proliferation

B cell lymphoma cell KARPAS422 was cultured using standard cell culture conditions in RPMI-1640 (Invitrogen, cat #11875) supplemented with 15% FBS (Invitrogen, cat #10099-141) in humidified incubator at 37° C., 5% $CO_2$. To assess the effect of PRC2 inhibition on cell proliferation, exponentially growing cells were seeded at a density of $1 \times 10^5$ cells/mL in 12-well plate (Corning, cat #CLS3513). After cell seeding, a compound of the present invention was added to the cell media (in concentrations ranging from 0 to 100 µM, 3× dilution series). Viable cell numbers were determined every 3-4 days for up to 14 days using Vi-CELL (Beckman Coulter). On days of cell counting, fresh growth media and compound were replenished and cells split back to a density of $1 \times 10^5$ cells/mL. Total cell number is expressed as split-adjusted viable cells per mL. The dose response curves and $IC_{50}$ values were generated using Prism.

Analysis of Pharmacokinetic Properties

Pharmacokinetic properties of the compounds as presently disclosed can be determined by using the below described protocol.

A representative compound of the present invention was dissolved in 10% PEG300, 10% Solutol HS 15 and 80% pH 4.65 Acetate buffer to yield a final concentration of 0.2 mg/mL for intravenous (IV) and oral administration (PO).

For rat PK studies, a total of three male Sprague Dawley rats each were used for rat IV and PO PK study, respectively. The formulation solution was administered via a single bolus IV at 1 mg/kg and a single oral gavage (PO) at 2 mg/kg, respectively. Blood samples (approximately 150 µL) were collected via jugular cannula at appropriate time points.

For mouse PK study, a total of twelve male ICR mice were used for IV and PO study, respectively. The formulation solution was administered via a single bolus IV at 1 mg/kg and a single oral gavage (PO) at 2 mg/kg, respectively. Blood samples (approximately 150 µL) were collected via retro-orbital puncture (~150 µL/mouse) after anesthetized by isoflurane or via cardiac puncture (terminal collection) at appropriate time points (n=3).

Samples were collected in tubes containing K3-EDTA and stored on ice until centrifuged. The blood samples were centrifuged at approximately 8000 rpm for 6 min at 2-8° C. and the resulting plasma was separated and stored frozen at approximately –80° C. After adding the internal standard, the plasma samples were quantified by LC-MS/MS using the calibration curve. PK parameters including area under concentration curve (AUC), mean residence time (MRT), plasma clearance (Cl), steady state volume of distribution (Vdss), elimination half-life ($t_{1/2}$), maximum concentration (Cmax), time of maximum concentration (Tmax) and oral bioavailability (F %) were calculated using the following equations:

$$AUC = \int_0^\infty C\, dt$$

$$MRT = \frac{\int_0^\infty tC\, dt}{\int_0^\infty C\, dt} = \frac{AUMC}{AUC}$$

t is time and C is plasma concentration at the time (t); $Dose_{iv}$ is the dose for intravenous administration; and $Dose_{oral}$ is the dose for oral administration.

$Cl = Dose_{iv}/AUC$ $t_{1/2} = 0.693 \times MRT$ $Vdss = Cl \ast MRT$ $F\% = (Dose_{iv} \times AUC_{oral})/Dose_{oral} \times AUC_{iv}) \times 100\%$ Protocol for High-Throughput Equilibrium Solubility Assay Compounds of the present invention were first solubilized at 10 mM in pure DMSO. 20 µL each of the DMSO stock solution was then transferred into 6 wells on 96-well plate. The DMSO solvent was dried with GeneVac solvent evaporator at 30° C., 1 mbar vacuum for 1 h. After the addition of 200 µL of buffer solutions (pH 6.8, or FaSSIF), the plate was sealed and shaken at 160 rpm for 24 h at rt. The plate was centrifuged at 3750 rpm for 20 min, 5 µL of supernatant is mixed with 495 µL of MeOH/H$_2$O (1:1). 0.01 µM, 0.1 µM, 1 µM, 10 µM stock solutions were prepared by series of dilution for the calibration curves. The supernatant was quantified by HPLC or LC/MS using the calibration curve. High-Throughput equilibrium solubility was determined based on the concentration of the supernatant.

Efficacy Studies in Mouse Xenograft Model

All experiments conducted were performed in female athymic Nude-nu mice in an AAALAC certificated facility. The animals were kept under SPF conditions in individual ventilation cages at constant temperature and humidity (i.e., 20-26° C.; 40-70%) with 5 or less animals in each cage. Animals had free access to irradiation sterilized dry granule food and sterile drinking water. All procedures and protocols were approved by the Institutional Animal Care and Use.

The cells Karpas 422 human B cell lymphoma were cultured in RPMI-1640 medium (Gibco; 11875-093) supplemented with 15% FBS (Gibco; 10099-141) and 1% Pen Strep (Gibco; 15140-122) at 37° C. in an atmosphere of 5% CO$_2$ in air. Cells were maintained in suspension cultures at concentrations between 0.5-2×10$^6$ cells/ml. Cells were split at 1:3 every 2-4 days. To establish xenograft tumor models the cells were collected, suspended in PBS, mixed with Matrigel (BD Bioscience) at a volume ratio of 1:1 at a concentration of 1×10$^8$ cells/mL and then injected subcutaneously into the right flank of balb/c nude mice (Vital River) at a concentration of 5×10$^6$ cells per animal.

The compound was formulated as a suspension in 0.5% methyl cellulose (MC) and 0.5% Tween 80 in 50 mM pH6.8 buffer (prepared in house according to the USP) and administered orally by gavage at specific doses.

Treatment was initiated when the average tumor volume reached 100-300 mm$^3$. Tumor growth and body weights were monitored at regular intervals. The two largest diameters, width (W) and length (L), of the xenograft tumors were measured manually with calipers and the tumor volume was estimated using the formula: $0.5 \times L \times W^2$.

When applicable, results are presented as mean±SEM. Graphing and statistical analysis was performed using GraphPad Prism 5.00 (GraphPad Software). Tumor and body weight change data were analyzed statistically. If the variances in the data were normally distributed (Bartlett's test for equal variances), the data were analyzed using one-way ANOVA with post hoc Dunnet's test for comparison of treatment versus control group. The post hoc Tukey test was used for intragroup comparison. Otherwise, the Kruskal-Wallis ranked test post hoc Dunn's was used.

As a measure of efficacy the % T/C value is calculated at the end of the experiment according to:

($\Delta$tumor volume$^{treated}$/$\Delta$tumor volume$^{control}$)*1100

Tumor regression was calculated according to:

–($\Delta$tumor volume$^{treated}$/tumor volume$^{treated\ at\ start}$)*100

Where $\Delta$tumor volumes represent the mean tumor volume on the evaluation day minus the mean tumor volume at the start of the experiment.

N-((5-fluoro-2,3-dihydrobenzofuran-4-yl)methyl)-8-(2-methylpyridin-3-yl)-[1,2,4]triazolo[4,3-c]pyrimidin-5-amine was tested in the EED (a) Alphascreen binding Qualified, (b) LC-MS Qualified and (c) ELISA Qualified assays described above and found to have EED inhibitory activity.

| IUPAC name | (a) IC$_{50}$ (µM) | (b) IC$_{50}$ (µM) | (c) IC$_{50}$ (µM) |
|---|---|---|---|
| N-((5-fluoro-2,3-dihydrobenzofuran-4-yl)methyl)-8-(2-methylpyridin-3-yl)-[1,2,4]triazolo[4,3-c]pyrimidin-5-amine | 0.0059 | 0.0089 | 0.0026 |

The antiproliferative activities (IC$_{50}$ values) in B cell lymphoma cell KARPAS422 after 14 days of treatment for N-((5-fluoro-2,3-dihydrobenzofuran-4-yl)methyl)-8-(2-methylpyridin-3-yl)-[1,2,4]triazolo[4,3-c]pyrimidin-5-amine is 0.0030 µM.

Accordingly, N-((5-fluoro-2,3-dihydrobenzofuran-4-yl)methyl)-8-(2-methylpyridin-3-yl)-[1,2,4]triazolo[4,3-c]pyrimidin-5-amine has been found to inhibit EED and is therefore useful in the treatment of diseases or disorders associated with EED and PRC2, which include, but are not limited to, diffused large B cell lymphoma (DLBCL), follicular lymphoma, other lymphomas, leukemia, multiple myeloma, mesothelioma, gastric cancer, malignant rhabdoid tumor, hepatocellular carcinoma, prostate cancer, breast carcinoma, bile duct and gallbladder cancers, bladder carcinoma, brain tumors including neurobalstoma, glioma, glioblastoma and astrocytoma, cervical cancer, colon cancer, melanoma, endometrial cancer, esophageal cancer, head and neck cancer, lung cancer, nasopharhyngeal carcinoma, ovarian cancer, pancreatic cancer, renal cell carcinoma, rectal cancer, thyroid cancers, parathyroid tumors, uterine tumors, and soft tissue sarcomas selected from rhabdomyosarcoma (RMS), Kaposi sarcoma, synovial sarcoma, osteosarcoma and Ewing's sarcoma.

V. PHARMACEUTICAL COMPOSITIONS AND COMBINATIONS

A "pharmaceutically acceptable carrier (diluent or excipient)" refers to media generally accepted in the art for the delivery of biologically active agents to animals, in particular, mammals, including, generally recognized as safe (GRAS) solvents, dispersion media, coatings, surfactants, antioxidants, preservatives (e.g., antibacterial agents, antifungal agents), isotonic agents, absorption delaying agents, salts, preservatives, drug stabilizers, binders, buffering agents (e.g., maleic acid, tartaric acid, lactic acid, citric acid, acetic acid, sodium bicarbonate, sodium phosphate, and the like), disintegration agents, lubricants, sweetening agents, flavoring agents, dyes, and the like and combinations thereof, as would be known to those skilled in the art (see, for example, Allen, L. V., Jr. et al., Remington: The Science and Practice of Pharmacy (2 Volumes), 22nd Edition, Pharmaceutical Press (2012). The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above.

Compound X can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

Compound X is typically formulated into pharmaceutical dosage forms to provide an easily controllable dosage of the drug and to give the patient an elegant and easily handleable product. The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. Compound X may be administered in a single daily dose, or the total daily dosage may be administered in divided doses of two, three, or four times daily.

In certain instances, it may be advantageous to administer Compound X in combination with at least one additional pharmaceutical (or therapeutic) agent, such as other anti-cancer agents, immunomodulators, anti-allergic agents, anti-nausea agents (or anti-emetics), pain relievers, cytoprotective agents, and combinations thereof.

The term "combination therapy" refers to the administration of two or more therapeutic agents to treat a therapeutic disease, disorder or condition described in the present invention. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Compound X and additional therapeutic agents can be administered via the same administration route or via different administration routes. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with Compound X may include:cyclin-dependent kinase (CDK) inhibitors, checkpoint kinase (CHK) inhibitors, C-RAF inhibitors, phosphoinositide 3-kinase (PI3K) inhibitors, BCL-2 inhibitors, mitogen-activated protein kinase (MEK) inhibitors, topoisomerase II inhibitors, SRC inhibitors, histone deacetylase (HDAC) inhibitors, anti-tumor antibiotics, demethylating agents, and anti-estrogens.

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids (Knutson, S., et al., PLoS One, DOI:10.1371/journal.pone.0111840 (2014)), such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methyl-prednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Immunomodulators of particular interest for combinations with the compounds of the present invention include one or more of: an activator of a costimulatory molecule or an inhibitor of an immune checkpoint molecule (e.g., one or more inhibitors of PD-1, PD-L1, LAG-3, TIM-3 or CTLA4) or any combination thereof.

In certain embodiments, the immunomodulator is an activator of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In certain embodiments, the immunomodulator is an inhibitor of an immune checkpoint molecule. In one embodiment, the immunomodulator is an inhibitor of PD-1, PD-L1, PD-L2, CTLA4, TIM3, LAG3, VISTA, BTLA, TIGIT, LAIR1, CD160, 2B4 and/or TGFR beta. In one embodiment, the inhibitor of an immune checkpoint molecule inhibits PD-1, PD-L1, LAG-3, TIM-3 or CTLA4, or any combination thereof. The term "inhibition" or "inhibitor" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40% or more is included by this term. Thus, inhibition need not be 100%.

Some patients may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g. Patents International (e.g. IMS World Publications).

In one embodiment, the present invention provides pharmaceutical compositions comprising Compound X together with a pharmaceutically acceptable carrier suitable for administration to a human or animal subject, either alone or together with other anti-cancer agents.

In one embodiment, the present invention provides methods of treating human or animal subjects suffering from a cellular proliferative disease, such as cancer. The present invention provides methods of treating a human or animal subject in need of such treatment, comprising administering to the subject a therapeutically effective amount of a compound of the present invention (e.g., a compound of the present invention) or a pharmaceutically acceptable salt thereof, either alone or in combination with other anti-cancer agents.

In particular, compositions will either be formulated together as a combination therapeutic or administered separately.

In combination therapy for treatment of a malignancy, Compound X and other anti-cancer agent(s) may be administered simultaneously, concurrently or sequentially with no specific time limits, wherein such administration provides therapeutically effective levels of the two compounds in the body of the subject.

In a preferred embodiment, Compound X and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include Compound X and a combination partner as disclosed herein are provided. Representative kits include (a) Compound X, (b) at least one combination partner, e.g., as indicated above, whereby such kit may comprise a package insert or other labeling including directions for administration.

Compound X may also be used to advantage in combination with known therapeutic processes, for example, the administration of hormones or especially radiation. Compound X may in particular be used as a radiosensitizer, especially for the treatment of tumors which exhibit poor sensitivity to radiotherapy.

In another aspect of the present invention, kits that include Compound X and a combination partner as disclosed herein are provided. Representative kits include (a) Compound X, (b) at least one combination partner, e.g., as indicated above, whereby such kit may comprise a package insert or other labeling including directions for administration.

In the combination therapies of the invention, Compound X and the other therapeutic agent may be manufactured and/or formulated by the same or different manufacturers. Moreover, Compound X and the other therapeutic (or pharmaceutical agent) may be brought together into a combination therapy: (i) prior to release of the combination product to physicians (e.g. in the case of a kit comprising Compound X and the other therapeutic agent); (ii) by the physician themselves (or under the guidance of the physician) shortly before administration; (iii) in the patient themselves, e.g. during sequential administration of Compound X and the other therapeutic agent.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

What is claimed is:

1. A hydrated solid form of N-((5-Fluoro-2,3-dihydrobenzofuran-4-yl)methyl)-8-(2-methylpyridin-3-yl)-[1,2,4]triazolo[4,3-c]pyrimidin-5-amine hydrochloride wherein, i) the hydrated solid form of N-((5-Fluoro-2,3-dihydrobenzofuran-4-yl)methyl)-8-(2-methylpyridin-3-yl)-[1,2,4]triazolo[4,3-c]pyrimidin-5-amine hydrochloride has a X-ray powder diffraction pattern comprising the following 2θ values (CuKα λ=1.5418 Å): 13.8±0.1, 20.8±0.1, 26.2±0.1, 26.7±0.1, and 28.2±0.1 or ii) the hydrated solid form of N-((5-Fluoro-2,3-dihydrobenzofuran-4-yl)methyl)-8-(2-methylpyridin-3-yl)-[1,2,4]triazolo[4,3-c]pyrimidin-5-amine hydrochloride has a X-ray powder diffraction pattern comprising the following 2θ values (CuKα λ=1.5418 Å): 9.0±0.1, 17.1±0.1, 22.8±0.1, 26.9±0.1, and 35.3±0.1.

2. A pharmaceutical composition, comprising one or more pharmaceutically acceptable carriers and a hydrated solid form of N-((5-Fluoro-2,3-dihydrobenzofuran-4-yl)methyl)-8-(2-methylpyridin-3-yl)-[1,2,4]triazolo[4,3-c]pyrimidin-5-amine hydrochloride, wherein, i) the hydrated solid form of N-((5-Fluoro-2,3-dihydrobenzofuran-4-yl)methyl)-8-(2-methylpyridin-3-yl)-[1,2,4]triazolo[4,3-c]pyrimidin-5-amine hydrochloride has a X-ray powder diffraction pattern comprising the following 2θ values (CuKα λ=1.5418 Å): 13.8±0.1, 20.8±0.1, 26.2±0.1, 26.7±0.1, and 28.2±0.1 or ii) the hydrated solid form of N-((5-Fluoro-2,3-dihydrobenzofuran-4-yl)methyl)-8-(2-methylpyridin-3-yl)-[1,2,4]triazolo[4,3-c]pyrimidin-5-amine hydrochloride has a X-ray powder diffraction pattern comprising the following 2θ values (CuKα λ=1.5418 Å): 9.0±0.1, 17.1±0.1, 22.8±0.1, 26.9±0.1, and 35.3±0.1.

3. The pharmaceutical composition of claim 2 further comprising at least one additional therapeutic agent.

4. The pharmaceutical composition of claim 3 where the at least one additional therapeutic agent is selected from an anti-cancer agent, an immunomodulator, an anti-allergic agent, an anti-emetic, a pain reliever and a cytoprotective agent.

* * * * *